(12) United States Patent
Singh et al.

(10) Patent No.: US 9,291,585 B2
(45) Date of Patent: Mar. 22, 2016

(54) APPARATUS AND METHOD FOR PHASE EQUILIBRIUM WITH IN-SITU SENSING

(75) Inventors: Anil Singh, Houston, TX (US); Kurt Schmidt, Oxford (GB); Brian Abbott, Edmonton (CA); Robert J Schroeder, Newtown, CT (US); Eric Paul Donzler, Bercheres sur Vesgre (FR)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 591 days.

(21) Appl. No.: 13/818,996

(22) PCT Filed: May 17, 2011

(86) PCT No.: PCT/IB2011/052145
§ 371 (c)(1),
(2), (4) Date: Jun. 6, 2013

(87) PCT Pub. No.: WO2012/025840
PCT Pub. Date: Mar. 1, 2012

(65) Prior Publication Data
US 2013/0243028 A1    Sep. 19, 2013

Related U.S. Application Data

(60) Provisional application No. 61/377,167, filed on Aug. 26, 2010.

(51) Int. Cl.
*G01N 25/20* (2006.01)
*G01K 17/00* (2006.01)
(Continued)

(52) U.S. Cl.
CPC ............ *G01N 25/00* (2013.01); *G01N 33/2823* (2013.01); *G01N 9/002* (2013.01); *G01N 9/34* (2013.01); *G01N 11/04* (2013.01); *G01N 11/16* (2013.01)

(58) Field of Classification Search
USPC ...................... 374/31, 43, 208, 120, 141, 143
See application file for complete search history.

(56) References Cited

U.S. PATENT DOCUMENTS 4,280,823 A    7/1981    Szonntagh
4,302,965 A *  12/1981   Johnson ................. G01N 11/06
                                                              374/142

(Continued)

FOREIGN PATENT DOCUMENTS

EP    0364217    12/1995
EP    1804048    5/2010

(Continued)

OTHER PUBLICATIONS

Oag, et al., "Determining phase boundaries and vapour/liquid critical points in supercritical fluids: a multi-technique approach", The Journal of Supercritical Fluids, vol. 30, Issue 3, Aug. 2004, pp. 259-272.

(Continued)

*Primary Examiner* — Mirellys Jagan
(74) *Attorney, Agent, or Firm* — Robert A. Van Someren; Wayne I. Kanak

(57) ABSTRACT

A technique facilitates the monitoring of thermodynamic properties of reservoir fluids. The technique utilizes a modular sensor assembly designed to evaluate a sample of a hydrocarbon-containing fluid within a cell body. A variety of sensors may be selectively placed into communication with a sample chamber within the cell body to evaluate the sample at potentially high pressures and temperatures. The sensors may comprise a density-viscosity sensor located in-situ to efficiently measure both the density and viscosity of the sample as a function of pressure and temperature. Other sensors, such as an optic sensor, may also be positioned to measure parameters of the sample while the sample is retained in the sample chamber.

12 Claims, 25 Drawing Sheets

(51) Int. Cl.
| | |
|---|---|
| G01K 13/00 | (2006.01) |
| G01N 25/00 | (2006.01) |
| G01N 33/28 | (2006.01) |
| G01N 9/00 | (2006.01) |
| G01N 9/34 | (2006.01) |
| G01N 11/04 | (2006.01) |
| G01N 11/16 | (2006.01) |

(56) References Cited

U.S. PATENT DOCUMENTS

| | | | |
|---|---|---|---|
| 4,395,902 | A | 8/1983 | Espenscheid et al. |
| 4,398,925 | A | 8/1983 | Trinh et al. |
| 4,425,810 | A * | 1/1984 | Simon .............. G01N 21/03 374/45 |
| 4,530,234 | A | 7/1985 | Cullick et al. |
| 4,688,436 | A | 8/1987 | Richon et al. |
| 4,783,989 | A | 11/1988 | Reed et al. |
| 4,994,671 | A | 2/1991 | Safinya et al. |
| 5,030,012 | A * | 7/1991 | Hagins ............. G01N 25/482 374/31 |
| 5,166,747 | A | 11/1992 | Schroeder et al. |
| 5,213,763 | A | 5/1993 | Pucci et al. |
| 5,536,474 | A | 7/1996 | Ungerer et al. |
| 5,540,087 | A | 7/1996 | Bickert et al. |
| 5,747,674 | A | 5/1998 | Moracchini et al. |
| 5,756,884 | A | 5/1998 | Moracchini et al. |
| 5,770,795 | A | 6/1998 | Behar et al. |
| 6,568,248 | B1 | 5/2003 | Guieze et al. |
| 6,966,228 | B2 | 11/2005 | Binet et al. |
| 7,434,457 | B2 | 10/2008 | Goodwin et al. |
| 7,574,898 | B2 | 8/2009 | Harrison et al. |
| 7,628,058 | B2 | 12/2009 | Legrand et al. |
| 8,564,768 | B2 | 10/2013 | Schroeder et al. |
| 2007/0035737 | A1 | 2/2007 | Andrews et al. |
| 2008/0156093 | A1 | 7/2008 | Permuy et al. |
| 2008/0257036 | A1 | 10/2008 | Chaudoreille et al. |
| 2009/0052273 | A1 | 2/2009 | Sarvazyan et al. |
| 2009/0120168 | A1 | 5/2009 | Harrison et al. |
| 2009/0166032 | A1 | 7/2009 | Carr |
| 2009/0211364 | A1 | 8/2009 | Lindeberg et al. |
| 2010/0265492 | A1 | 10/2010 | Schroeder et al. |
| 2013/0243028 | A1 | 9/2013 | Singh et al. |
| 2015/0285690 | A1* | 10/2015 | van Houten .............. G01K 7/16 374/103 |

FOREIGN PATENT DOCUMENTS

| | | |
|---|---|---|
| GB | 2188437 A | 9/1987 |
| GB | 2304906 | 3/1997 |
| RU | 2201503 C2 | 3/2003 |
| RU | 2349751 C2 | 3/2009 |
| RU | 2383734 C2 | 3/2010 |
| RU | 2392430 C2 | 6/2010 |
| WO | 99/00575 | 1/1999 |
| WO | 2007027100 A1 | 3/2007 |
| WO | 2012025840 A2 | 3/2012 |

OTHER PUBLICATIONS

Outcalt, et al., "A small-volume apparatus for the measurement of phase equilibria", National Institute of Standards and Technology, vol. 109, No. 6, Nov.-Dec. 2004, 7 pages.
Paso, et al., "Measurement of Wax Appearance Temperature Using Near-Infrared (NIR) Scattering", Energy Fuels, vol. 23, No. 10, 2009, pp. 4988-4994.
Peleties, et al., "Circulating pump for high-pressure and high-temperature applications", Review of Scientific Instruments, vol. 76, 2005, p. 105103.
Rivollet, et al., "PpT and VLE for Ethane + Hydrogen Sulfide from (254.05 to 363.21) K at Pressures up to 20 MPa", Journal of Chemical & Engineering Data, vol. 50, No. 6, Oct. 19, 2005, pp. 1883-1890.
Sanmamed, et al., "Viscosity-induced errors in the density determination of room temperature ionic liquids using vibrating tube densitometry", Fluid Phase Equilibria, vol. 252, Issues 1-2, Mar. 1, 2007, pp. 96-102.
Sivaraman, et al., "Acoustic Dew Point and Bubble Point Detector for Gas Condensates and Reservoir Fluids", PETSOC-97-80, Petroleum Society of Canada, Annual Technical Meeting, Calgary, Alberta, Jun. 8-11, 1997, 7 pages.
Smits, "In-Situ Optical Fluid Analysis as an Aid to Wireline Formation Sampling", SPE Formation Evaluation, vol. 10, No. 2, Jun. 1995, pp. 91-98.
Stenby, et al., "A new apparatus for studies of near critical hydrocarbon fluids: Part I: PVT, density, and viscosity", Fluid Phase Equilibria, vol. 82, Feb. 1993, pp. 149-156.
Tekáč, et al., "PVT properties of liquids and liquid mixtures: a review of the experimental methods and the literature data", Fluid Phase Equilibria, vol. 19, Issues 1-2, 1985, pp. 33-149.
Turek, et al., "Phase Equilibria in CO2—Multicomponent Hydrocarbon Systems: Experimental Data and an Improved Prediction Technique", SPE-9231-PA, Society of Petroleum Engineers, vol. 24, Issue 3, Jun. 1984, pp. 308-324.
Valtz, et al., "ROLSI®: Rapid On-Line Sampler-Injector, a new tool for sampling and on-line GC analysis in a large range of pressures and temperatures", ARMINES Publication, Retrieved online: http://www.ensmp.fr/~richon.
Van Doorn, et al., "High pressure circulating pump", Review of Scientific Instruments, vol. 73 Issue 11, Nov. 2002, p. 4037.
Yang, et al., "Phase behavior of a near-critical reservoir fluid mixture", Fluid Phase Equilibria, vol. 128, Issues 1-2, Feb. 15, 1997, pp. 183-197.
Zhuang, et al., "An automated high pressure PVT apparatus for continuous recording of density and isothermal compressibility of fluids", Review of Scientific Instruments, vol. 67, No. 1, 1996, p. 244.
Ahmed, "Equations of State and PVT Analysis", Gulf Publishing Company, ISBN-13: 978-1933762036, Feb. 15, 2007, pp. 260-307.
Danesh, "PVT and Phase Behaviour of Petroleum Reservoir Fluids", Elsevier, ISBN: 978-0-444-82196-6, May 1998, pp. 33-104.
Muhlbauer, et al., "Phase Equilibria: Measurement & Computation", CRC Press, ISBN:978-1560325505, Sep. 1, 1997, Chapters 2,3,6,7,8 and 9.
Pedersen, et al., "Phase Behavior of Petroleum Reservoir Fluids", Boca Raton : CRC/Taylor & Francis, 2007, pp. 41-62.
Whitson, et al., "Phase Behavior", Society of Petroleum Engineers, SPE Monograph Series vol. 20, ISBN:978-1-55563-087-4, 2000, 233 pages.
International Search Report and Written Opinion issued in PCT/IB2011/052145 on Feb. 27, 2013, 66 pages.
International Preliminary Report on Patentability issued in PCT/IB2011/052145 on Mar. 12, 2013, 6 pages.
Examination Report issued AU2011294831 on Jul. 23, 2013, 3 pages.
Office Action issued in MX/A/2013/002213 on Sep. 18, 2013, 7 pages.
Office Action issued in RU2013113218 on Oct. 27, 2014, 11 pages.
Examiner's Report issued in CA2809612 on Nov. 14, 2014, 5 pages.
Written Opinion issued in SG201301349-5 on Jul. 17, 2014, 8 pages.
Office Action issued in MX/A/2013/002213 on Feb. 27, 2015, 7 pages.
Armines, "Rolsi", Retrieved online: http://www.armines.net/rolsi_155.php.
Clear Examination Report issued in SG2013013495 on Jul. 7, 2015, 7 pages.
Office action for the equivalent Singapore patent application No. 201301349-5 issued on Nov. 26, 2013.
Abramov, et al., "High-Intensity Ultrasonics: Theory and Industrial Applications", Chapter 2; Gordon and Breach, 1998, pp. 67-160.
Alex, et al., "Determination of cloud point for waxy crudes using a near-infrared/fiber optic technique", Energy Fuels, vol. 5, No. 6, 1991, pp. 866-868.
Al-Meshari, et al., "Near-Critical and Volatile Oil Densities and Viscosities at Reservoir Conditions", SPE-108434-MS, Society of Petroleum Engineers, SPE Annual Technical Conference and Exhibition, Anaheim, California, U.S.A., Nov. 11-14, 2007, 8 pages.

(56) References Cited

OTHER PUBLICATIONS

Aquino-Olivos, et al., "Investigations of Inhibition of Asphaltene Precipitation at High Pressure Using Bottomhole Samples", Energy Fuels, vol. 15, No. 1, 2001, pp. 236-240.
Assael, et al., "An absolute vibrating-wire viscometer for liquids at high pressures", International Journal of Thermophysics, vol. 12, Issue 2, 1991, pp. 231-244.
Audonnet, et al., "Simultaneous measurement of density and viscosity of n-pentane from 298 to 383 K and up to 100 MPa using a vibrating-wire instrument", Fluid Phase Equilibria, vol. 181, Issues 1-2, May 25, 2001, pp. 147-161.
Badry, et al., "Downhole Optical Analysis of Formation Fluids", Oilfield Review, vol. 6, Issue 1, Jan. 1994, pp. 21-28.
Besserer, et al., "A high pressure autocollimating refractometer for determining coexisting liquid and vapor phase densities", The Canadian Journal of Chemical Engineering, vol. 49, Issue 5, Oct. 1971, pp. 651-656.
Bouchot, et al., "Direct Pressure-Volume-Temperature and Vapor-Liquid Equilibrium Measurements with a Single Equipment Using a Vibrating Tube Densimeter up to 393 K and 40 MPa: Description of the Original Apparatus and New Data", Industrial & Engineering Chemistry Research, vol. 37, No. 8, 1998, pp. 3295-3304.
Caudwell, et al., "A robust vibrating wire viscometer for reservoir fluids: results for toluene and n-decane", Journal of Petroleum Science and Engineering, vol. 44, Issues 3-4, Nov. 15, 2004, pp. 333-340.
Caudwell, et al., "The viscosity and density of n-dodecane and n-octadecane at pressures up to 200 MPa and temperatures up to 473 K", International Journal of Thermophysics, vol. 25, No. 5, 2004, pp. 1339-1352.
Caudwell, et al., "Viscosity and Density of Five Hydrocarbon Liquids at Pressures up to 200 MPa and Temperatures up to 473 K", Journal of Chemical & Engineering Data, vol. 54, No. 2, 2009, pp. 359-366.
Christov, et al., "High-pressure fluid phase equilibria: Experimental methods and systems investigated (1994-1999)", Fluid Phase Equilibria, vol. 202, Issue 1, Oct. 15, 2002, pp. 153-218.
Colgate, et al., "Acoustic cavity method for phase boundary determinations: The critical temperature of CO2", Review of Scientific Instruments, vol. 62, No. 1, 1991.
Colgate, et al., "Acoustic resonance determination of sonic speed and the critical point for a typical retrograde gas condensate", Fluid Phase Equilibria, vol. 79, Nov. 25, 1992, pp. 231-240.
Comuñas, et al., "Density of Diethyl Adipate using a New Vibrating Tube Densimeter from (293.15 to 403.15) K and up to 140 MPa. Calibration and Measurements", Journal of Chemical Engineering, vol. 53, No. 4, Mar. 22, 2008, pp. 986-994.
Dahl, et al., "Compositional Analysis of Oil Samples at High Pressure", Industrial & Engineering Chemistry Research, vol. 38, No. 2, 1999, pp. 562-564.
Dandekar, et al., "Measurement of Phase Behavior of Hydrocarbon Mixtures Using Fiber Optical Detection Techniques", SPE-38845-MS, Society of Petroleum Engineers, SPE Annual Technical Conference and Exhibition, San Antonio, Texas, Oct. 5-8, 1997.
Dandekar, et al., "Measurement of Phase Boundaries of Hydrocarbon Mixtures Using Fiber Optical Detection Techniques", Industrial & Engineering Chemistry Research, vol. 39, No. 7, 2000, pp. 2586-2591.
Danesh, et al., "A novel sampling method for compositional analysis of high pressure fluids", Fluid Phase Equilibria, vol. 57, Issues 1-2, 1990, pp. 161-171.
Dohrn, et al., "High-pressure fluid-phase equilibria: Experimental methods and systems investigated (1988-1993)", Fluid Phase Equilibria, vol. 106, Issues 1-2, May 1, 1995, pp. 213-282.
Dohrn, et al., "High-pressure fluid-phase equilibria: Experimental methods and systems investigated (2000-2004)", Fluid Phase Equilibria, vol. 288, Issues 1-2, Jan. 25, 2010, pp. 1-54.
Etchart, et al., "Operation of a Vibrating Wire Viscometer with a Wire Radius of 0.207 mm in a Fluid with Nominal Viscosity, at T =289.1 K, of 1.581 Pa•s at Temperatures between (289.1 and 420.7) K and a Pressure of 0.1 MPa", Journal of Chemical & Engineering Data, vol. 52, No. 4, 2007, pp. 1494-1496.
Ewing, et al., "Relative permittivitties and dielectric virial coefficients of nitrogen at T=283.401K and T=303.409K determined using a cylindrical microwave cavity resonator", The Journal of Chemical Thermodynamics, vol. 34, 2002, pp. 1985-1999.
Folas, et al., "High-pressure vapor-liquid equilibria of systems containing ethylene glycol, water and methane: Experimental measurements and modeling", Fluid Phase Equilibria, vol. 251, Issue 1, Jan. 15, 2007, pp. 52-58.
Fontalba, et al., "Simultaneous determination of vapor-liquid equilibria and saturated densities up to 45 MPa and 433 K", Review of Scientific Instruments, vol. 55, 1984, pp. 944-951.
Fornari, "High pressure fluid phase equilibria: experimental methods and systems investigated (1978-1987)", Fluid Phase Equilibria, vol. 57, Issues 1-2, 1990, pp. 1-33.
Frorup, et al., "High pressure dew and bubble points from microwave measurements", Fluid Phase Equilibria, vol. 52, Dec. 1989, pp. 229-235.
Goodwin, "A MEMS Vibrating Edge Supported Plate for the Simultaneous Measurement of Density and Viscosity: Results for Argon, Nitrogen, and Methane at Temperatures from (297 to 373) K and Pressures between (1 and 62) MPa", Journal of Chemical & Engineering Data, vol. 54, No. 2, 2009, pp. 536-541.
Goodwin, et al., "A Vibrating Edge Supported Plate, Fabricated by the Methods of Micro Electro Mechanical System for the Simultaneous Measurement of Density and Viscosity: Results for Methylbenzene and Octane at Temperatures between (323 and 423) K and Pressures in the Range (0.1 to 68) MPa", Journal of Chemical & Engineering Data, vol. 51, No. 1, 2006, pp. 190-208.
Goodwin, et al., "A MEMS Vibrating Edge Supported Plate for the Simultaneous Measurement of Density and Viscosity: Results for Nitrogen, Methylbenzene, Water, 1-Propene,1,1,2,3,3,3-hexafluoro-oxidized-polymd, and Polydimethylsiloxane and Four Certified Reference Materials with Viscosities in the Range (0.038 to 275) mPas and Densities between (408 and 1834) kg•m-3 at Temperatures from (313 to 373) K and Pressures up to 60 MPa", Journal of Chemical & Engineering Data, vol. 53, No. 7, 2008, pp. 1436-1443.
Gozalpour, et al., "Vapour-liquid equilibrium compositional data for a model fluid at elevated temperatures and pressures", Fluid Phase Equilibria, vol. 208, Issues 1-2, Jun. 15, 2003, pp. 303-313.
Gozalpour, et al., "Vapour-liquid equilibrium volume and density measurements of a five-component gas condensate at 278.15-383.15 K", Fluid Phase Equilibria, vol. 206, Issues 1-2, Apr. 30, 2003, pp. 95-104.
Gozalpour, et al., "Viscosity and Density Data of Two North Sea Gas Condensate Samples at Temperatures to 423 K and Pressures to 140 MPa", Journal of Chemical & Engineering Data, vol. 46, No. 5, 2001, pp. 1305-1308.
Guilbot, et al., "Rapid on-line sampler-injector: a reliable tool for HT-HP sampling and on-line GC analysis", Analusis, vol. 28, No. 5, Jun. 2000, pp. 426-431.
Hammami, et al., "Asphaltene Precipitation from Live Oils: An Experimental Investigation of Onset Conditions and Reversibility", Energy Fuels, vol. 14, No. 1, 2000, pp. 14-18.
Hammami, "Paraffin Deposition From Crude Oils: Comparison of Laboratory Results to Field Data", SPE-38776-PA, Society of Petroleum Engineers Annual Technical Conference and Exhibitions, San Antonio, Texas, U.S.A., Oct. 5-8, 15 pages.
Hu, et al., "Wax Precipitation in Three Chinese Reservoir Oils under Carbon Dioxide (CO2) Injection", Energy Fuels, vol. 18, No. 4, 2004, pp. 1183-1186.
Jamaluddin, et al., "Laboratory Techniques to Measure Thermodynamic Asphaltene Instability", PETSOC—Feb. 7, 2004, Petroleum Society of Canada, Journal of Canadian Petroleum Technology, vol. 41, Issue 7, Jul. 2002, 9 pages.
Kandil, et al., "The development of a vibrating wire viscometer and a microwave cavity resonator for the measurement of viscosity, dew points, density, and liquid volume fraction at high temperature and pressure", PhD Thesis, University of Canterbury, 2005.

(56) References Cited

OTHER PUBLICATIONS

Ke, et al., "Method for Locating the Vapor-Liquid Critical Point of Multicomponent Fluid Mixtures Using a Shear Mode Piezoelectric Sensor", Analytical Chemistry, vol. 77, No. 1, 2005, pp. 85-92.

Kordikowski, et al., "Acoustic probing of phase equilibria in near-critical fluids", Fluid Phase Equilibria, vols. 150-151, Sep. 19998, pp. 493-499.

Kordikowski, et al., "Probing Vapor/Liquid Equilibria of Near-Critical Binary Gas Mixtures by Acoustic Measurements", The Journal of Physical Chemistry A, vol. 100, No. 22, 1996, pp. 9522-9526.

Lu, et al., "Phase comparison techniques for measuring liquid—liquid phase equilibrium", Review of Scientific Instruments, vol. 70, No. 4, 1999, pp. 2065-2068.

Lundstrum, et al., "Measurement of the Viscosity and Density of Two Reference Fluids, with Nominal Viscosities at $T = 298$ K and $p = 0.1$ MPa of (16 and 29) mPa•s, at Temperatures between (298 and 393) K and Pressures below 55 MPa", Journal of Chemical & Engineering Data, vol. 50, No. 4, 2005, pp. 1377-1388.

May, et al., "Density, dielectric constant and PVT measurements of a gas condensate fluid", Journal of Petroleum Science and Engineering, vol. 41, Issue 4, Feb. 2004, pp. 297-308.

Meskel-Lesavre, et al., "New variable volume cell for determining vapor-liquid equilibria and saturated liquid molar volumes by the static method", Industrial & Engineering Chemistry Fundamentals, vol. 20, No. 3, Aug. 1981, pp. 284-289.

Morch, et al., "Measurement and modeling of hydrocarbon dew points for five synthetic natural gas mixtures", Fluid Phase Equilibria, vol. 239, Issue 2, Jan. 31, 2006, pp. 138-145.

Novitskiy, et al., "A New Continuous Method for Performing Rapid Phase Equilibrium Measurements on Binary Mixtures Containing $CO_2$ or $H_2O$ at High Pressures and Temperatures", Journal of Chemical & Engineering Data, vol. 54, No. 5, Feb. 20, 2009, pp. 1580-1584.

Top Autoclave, "ROLSI Sampler", Retrieved online: http://www.topautoclave.com/our-products/phases-equilibria-apparatus/.

International Search Report for the equivalent PCT patent application No. PCT/IB2011/052145 issued on Mar. 12, 2013.

\* cited by examiner

APPARATUS AND METHOD FOR PHASE EQUILIBRIUM WITH IN-SITU SENSING

CROSS-REFERENCE TO RELATED APPLICATION

The present application claims priority from U.S. Provisional Application 61/377,167, filed Aug. 26, 2010, which is incorporated herein by reference.

BACKGROUND OF THE INVENTION

In many oilfield applications, reservoir fluid samples are collected and thermodynamic studies and/or other studies are performed to obtain desired information on a subterranean reservoir. The thermodynamic studies involve measuring thermodynamic properties of reservoir fluids for phase behavior analysis and/or sample validation.

Phase behavior of reservoir fluids can be characterized using a plurality of apparatus types. Generally these devices are in the form of pressure retaining vessels capable of withstanding high temperatures and pressures. The pressure retaining vessels or cells use either mercury or pistons (in the case of mercury-free cells) to impart pressure onto the fluid sample via some type of displacement pump or mechanical drive. In mercury cells the immiscibility of the mercury with the sample is exploited to simplify the design, and no piston is required to impart pressure. Mercury has several obvious drawbacks and over the last several years the industry trend generally has been to move away from such designs. In the mercury-free cells, pressure is imparted on the sample fluid via a floating piston. The piston in turn is driven/moved either mechanically or hydraulically.

The pressure retaining cells are usually a visual type or blind type and are configured with sensors for measuring pressure and temperature. The cells may also work in cooperation with measuring instruments and/or sensors for measuring total sample volume, phase volumes, saturation pressures, and other parameters, either with the sensor or visually by an operator. In some cases ancillary external equipment can be configured in conjunction with the cells to make additional measurements such as density and viscosity, in which case a larger sample volume of fluid is required to make the additional measurements. Often, the external equipment can be operated in stand alone mode to make these measurements independent of the cell. The cells may have some mechanism for allowing a sample to be extracted during the experiment under equilibrium conditions via, for example, a sampling valve.

In addition to pressure management and experimental measurement sensors, the devices may have some type of thermal management system for temperature control, e.g. ovens or heating mantles/jackets. The equilibrium cell may also work in cooperation with a mechanism for agitating the sample. This is done to speed up the equilibrium process and hence increase experimental efficiency. The types of agitation mechanisms include magnetically coupled mechanical impeller type mixers, simple rocking mechanisms (with or without mixing rings), circulation pumps, and ultrasonic transducers.

The equilibrium cells are often designed specifically for the type of fluid under study. For example it is common to use a conical piston for the study of gas condensates and a flat piston for oils. The conical pistons are employed because the amount of liquid dropout from gas condensates is very small and by using conical pistons the capability of the apparatus to measure these very small volumes is enhanced.

Another trend to enhance the study of gas condensates is to use equilibrium cells with larger volumes than those used for oil studies. The rationale is that the larger the sample volume the greater the liquid dropout volume, which increases the likelihood of being within the measuring resolution of the instruments. One of the major drawbacks of these larger cells is the requirement of a larger sample volume.

Density and viscosity measurements may be performed by other pieces of equipment external to the main cell, e.g the PVT (pressure-volume-temperature) cell, or by incorporating a densitometer or viscometer into the apparatus. One common form of viscometer incorporated into the cell uses a capillary technique, and the most common form of densitometer is based on a vibrating tube technique. An example of such a densitometer is that made by Anton Paar GmbH of Graz, Austria. These measurement devices require that the sample is flowed/pushed through the viscometer or densitometer and, as such, require substantial sample volume to flow through the sensor for measurement and to flush/clean the sensors. These flow-through type sensors have many drawbacks, including a relatively large equipment footprint and sample volume requirement.

To determine phase volumes, most apparatus types measure the gas-liquid interface. The gas-liquid interface is formed as a result of being in a region of the phase envelope below the saturation point and having the gas and liquid layers stratified within the cell body. It is important that the gas phase and liquid phase be in equilibrium. Stratification will occur naturally, but this can take several hours, days, or weeks depending on the fluid system. In order to increase experimental efficiency, agitation is used to significantly reduce the time needed to reach equilibrium to the order of seconds or minutes. This requires the gas-liquid contact area to be maximized, sufficient gas-liquid retention time, and movement of both phases for the mass diffusion between the phases to be maximized at a given temperature and pressure.

When equilibrium is achieved the mass transfer of the individual components into each of the respective phases becomes zero. This is due to the conditions of thermodynamic equilibrium where the temperature and pressures of each phase are identical and the chemical potentials or fugacities of each component within each phase also become identical. An agitation or mixing technique is the standard technique used for decreasing approach times to equilibrium, the most effective being recirculation of one phase thorough the other. Agitation systems are varied, and include magnetically driven mixing rings/pistons/devices, simple cell rocking, a combination of mixing rings/pistons/devices and rocking, magnetically coupled impeller mixers, magnetic stirrers, static mixers, orifice mixers, circulation pumps, and ultrasonic stirrers (clamp-on externally mounted or transducer direct contact types).

In any case, existing devices lack sufficient sensor capabilities or combinations of sensor capabilities to enable sufficient phase behavior and sample validation studies of reservoir fluids.

BRIEF SUMMARY OF THE INVENTION

In general, the present invention provides an apparatus and method related to measuring thermodynamic properties of reservoir fluids. The technique utilizes a modular sensor assembly designed to evaluate a sample of a hydrocarbon containing fluid within a cell body. A variety of sensors may be selectively placed into communication with a sample chamber within the cell body to evaluate the sample at potentially high pressures and temperatures. By way of example, the sensors may comprise a single density-viscosity sensor located in-situ to efficiently measure both the density and viscosity of the sample as a function of pressure and temperature. Other sensors, such as an optic sensor and/or a pressure-temperature sensor, may also be positioned to measure parameters of the sample while the sample is retained in the sample chamber.

BRIEF DESCRIPTION OF THE DRAWINGS

Certain embodiments of the invention will hereafter be described with reference to the accompanying drawings, wherein like reference numerals denote like elements, and.

DETAILED DESCRIPTION OF THE INVENTION

Figure 1:
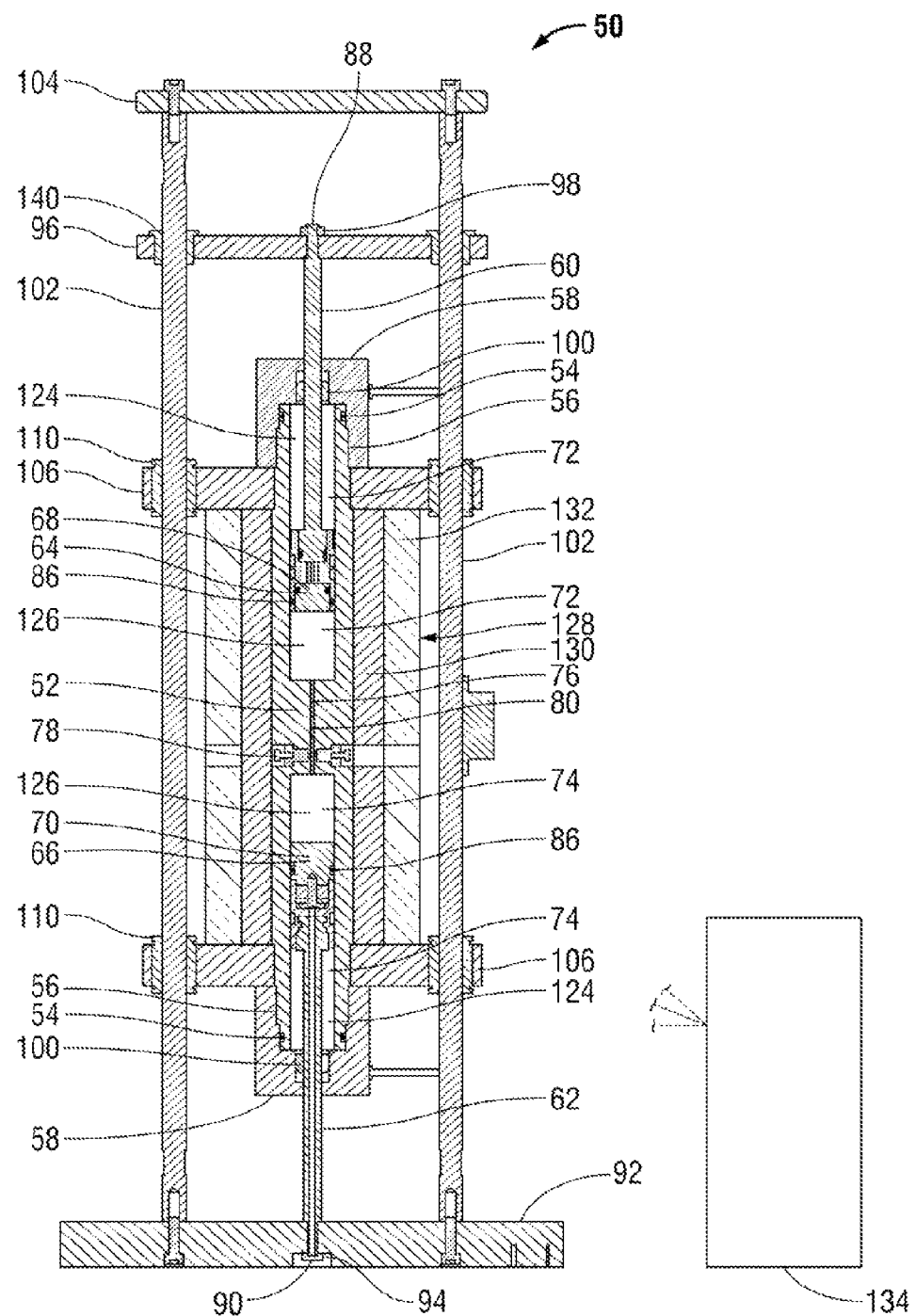
FIG. 1 is a schematic illustration of an example of a modular sensor assembly, according to an embodiment of the present invention.

In the following description, numerous details are set forth to provide an understanding of the present invention. However, it will be understood by those of ordinary skill in the art that the present invention may be practiced without these details and that numerous variations or modifications from the described embodiments may be possible.

The present invention relates to a method and system which enhances the overall service quality and data quality with respect to measurement and analysis of reservoir fluid samples. A variety of components are selectively integrated into a modular assembly to simplify the actions involved in measurement and analysis of the reservoir fluid samples. As a result, the reservoir fluid analysis process is more reliable and repeatable during many or all phases of the procedure. The system also is easily portable to wellsites and other desired locations.

As described herein, the invention relates to an apparatus for measuring thermodynamic properties (fluid properties, e.g. pressure-volume-temperature (PVT) and viscosity) of reservoir fluids for phase behavior studies and/or sample validation. These fluids may be obtained from a wellbore, from a downhole sampling tool, or from surface equipment, e.g. a separator.

Existing flow-through type sensors have the main drawbacks of relatively large equipment footprint and sample volume requirements. However, the modular sensor assembly embodiments described herein overcome these drawbacks by, for example, incorporating a single density-viscosity sensor as an integral part of the device, hence reducing the sample volume requirement and decreasing the equipment footprint. Reduced sample volume is preferred as the samples, especially those captured downhole, are expensive to obtain and are often available only in limited quantities. Hence, the present embodiments of the invention can generally perform more tests from a limited sample. Also, by reducing the equipment footprint, the assembly becomes more portable and better suited for deployment at the wellsite, especially offshore wellsites, where space is limited. The reduced footprint also means the equipment can be easily shipped from location to location, either on land or offshore, at minimal cost. The embodiments described herein may also be designed to eliminate the need for performing additional and separate testing, such as vapor-liquid equilibrium (VLE) experiments, separator tests (ST), differential liberation (DL) tests, and/or constant volume depletion (CVD) tests.

Additionally, the present modular sensor assembly and techniques for using the assembly are designed for use at higher pressures and temperatures than typical testing systems. In many of these applications, including the high pressure and high temperature applications, the hydrocarbon fluid sample is agitated to recombine the sample fluid from multiple phases into a single phase at pressures greater than the saturation pressure. The modular sensor assembly described herein may incorporate an integral agitator mechanism designed to agitate the fluid sample under high pressure and temperature.

Agitation of the sample is desired in many applications at about the saturation point after microbubbles/microdroplets are formed at nucleation sites and begin to grow due to, for example, diffusion. The ideal agitator should cause the growing bubbles/droplets to shear/breakup and form smaller bubbles/droplets, hence increasing the overall surface area and thus the gas-liquid contact area. As these bubbles/droplets grow, the ideal agitator should continually shear/break up the larger bubbles/droplets and also create a general flow circulation of the bubbles/droplets to avoid areas of low concentration gradients, hence lower mass diffusion rates. In liquid systems, the circulation from the ideal agitator allows the gas bubbles to move more quickly to the surface forming the interface than purely relying on the buoyancy effect. In the case of droplets, the ideal agitator causes them to fall to the bottom of the cell (top of the interface) much faster than reliance on gravity alone. At the same time and at the interface surface, the continuous flow circulation causes gas phase recirculation into the liquid phase or vice versa, hence allowing the stratified phases to contact each other and allowing for greater surface area contact between the phases, thus facilitating a faster diffusion process. This can be extended for recombination of the phases as well. The agitation technique and integrated agitation mechanism described below help optimize a desired agitation of the fluid sample. By way of example, the agitator mechanism may comprise an ultrasonic transducer which minimizes dead volume and incorporates easily into a cell body of the modular sensor assembly.

Embodiments described herein provide a modular sensor assembly in the form of an automated, mobile, and modular apparatus using new sensor technologies for phase behavior and sample validation studies of reservoir fluids. The modular portable apparatus is intended for use at the wellsite, onshore and offshore, mobile laboratory, or permanent shore-based laboratory locations. It can be used as either a standalone unit or in conjunction with other modular fluid analysis equipment.

In prior art systems, density and viscosity were usually measured by separate specialized devices such as a vibrating tube apparatus or gravimetric technique for density and falling body apparatus for viscosity. In DL and/or ST studies, the density of the co-existing liquid phase (liquid phase below the saturation pressure) was normally a calculated property and not a measured property. The viscosity of the co-existing liquid phases was often measured in a separate experiment with a separate charge of the fluid. In such case, the DL and/or ST study was replicated and the fluid then charged into the viscometer. These properties could also be measured in separate VLE studies, where a fresh sample is charged to the cell and then the co-existing liquid and vapor phases are sampled and the density, viscosity, and composition is measured. The data from the VLE, depending on the particular fluid, often did not match the DL, CVD or ST tests data exactly, but data from these VLE tests was still used in equation of state (EOS) tuning. Again, such tests were difficult to perform and consumed large amounts of sample volume and time. Depending on the experience of the operator, the results often had varying degrees of associated errors.

By contrast, embodiments of the present invention incorporate an in-situ combined density and viscosity sensor to measure single phase and coexisting two phase liquid phase densities and viscosities (but not limited to only the liquid phase) as a function of pressure and temperature. Integration of the combined density and viscosity sensor into the apparatus and experimental workflow eliminates the need to use separate pieces of equipment and separate sample charges into these external pieces of equipment, thus reducing experimental uncertainty and also reducing overall sample volume consumption. Fluid samples are expensive to obtain and hence the minimization of quantities used for testing has direct benefits, such as more sample availability for repeatability studies, more availability for a wider suite of tests, and the collection of smaller sample quantities (directly related to cost).

Drawbacks with existing techniques for making density and viscosity measurements during a phase equilibria experiment include: an increased sample volume and an experimental workflow which is more complicated as fluid normally has to flow through these sensors to make a measurement. It is even more complex when the fluid is in two phases because all the fluid in the sensors must be re-equilibrated at the new conditions of measurement and the sensor must be flushed thoroughly to ensure that the fluid sample is representative of the bulk liquid phase (hence consuming more sample volume). The present modular sensor assembly overcomes these issues and has a very simple experimental workflow.

For example, the present apparatus/assembly is highly autonomous and may be controlled via a processor-based control, such as a microcomputer. This approach requires minimal input from an operator. Through automation, the embodiments of the present invention ensure high quality, repeatable results which are largely independent of operator experience.

Another beneficial feature of the present modular sensor assembly and technique which may be incorporated into the modular design is a novel high pressure and high temperature optic sensor. The high pressure and high temperature optic sensor may be employed for making bubble point, dew point, gas-liquid interface measurements, and/or other measurements using optical spectroscopic and scattering techniques. The construction of the optic sensor avoids some of the drawbacks with sealing round or cylindrical type windows, and working in conjunction with the overall apparatus allows all the visual measurements typically made by an operator, in visual type cells, to be replaced with this sensor which allows for automation. The optical sensor is designed to enhance its sensitivity for detection of fine dew mists and small bubbles in the interrogation volume. Wavelengths and optical path lengths are optimized to enable detection of bubbles and gas-liquid interfaces even with dark crude hydrocarbons.

The modular design of embodiments of this invention also enable different configurations, cell geometries, and sensors to be used to study different fluid types. Reservoir fluids exhibit different behaviors (oil and gas condensates) in phase characterization studies. Also the fluid properties to be measured have a wide range. The ability to reconfigure the equipment and/or replace the sensors to fit the specific fluid type greatly reduces experimental uncertainty. The physics of the sensor and sensitivities may vary for oils and gas condensates, hence making it difficult, if not impossible, to use a single sensor which can maintain a very high degree of accuracy for all reservoir fluid types. The sensors and ranges, for very high accuracy measurements, can be customized for the fluid depending on whether it is an oil or a gas condensate. The modular sensor assembly is part of a modular hardware and software system used to ensure high quality and consistent quality analysis.

The assembly may be employed for other studies in addition to phase equilibria studies, with little or no modification. For example, the modular assembly may be used for sample validation purposes. Additionally, the modular sensor assembly may be used in conjunction with other modules. Validation tests typically measure or look for water content, sand, and other contamination levels. In some applications, validation testing may incorporate analysis techniques which are important in flow assurance studies, such as wax and asphaltene precipitation onset studies.

Referring generally to FIGS. 1-4, an embodiment of an apparatus for measuring thermodynamic properties of reservoir fluids is illustrated as a modular sensor assembly 50. The modular sensor assembly 50 comprises a cell body 52 constructed of, for example, a material resistant to corrosive wellbore fluids, e.g. water, hydrogen sulfide, and resistant to embrittlement and/or cracking with the capability of withstanding high pressures, e.g. 1380 bar minimum, and high temperatures, e.g. 200° C. minimum. The cell body 52 may be fabricated from a single piece of bar stock with sealing grooves 54 and threaded end connections 56 on each end so as to receive end caps 58.

The ends of the cell body 52 may be closed with the threaded end caps 58. Alternatively, end caps 58 may be bolted onto cell body 52 with a sealing groove. The threads or bolts are designed to resist the pressure and temperature loading. End caps 58 may be sealed onto the cell body 52 using an elastomeric or other type of seal in grooves 54. End caps 58 may also be employed to seal extended housing portions 60 and 62 which are disposed through respective ends of the cell body 52 for cooperation with a pressure and temperature sensor 64 and an agitator mechanism/sensor 66, such as an ultrasonic transducer. The pressure and temperature sensor 64 may be combined with an upper piston 68, and ultrasonic transducer 66 may be in the form of or integrated with a lower piston 70. It should be noted that upper piston 68 and/or lower piston 70 may incorporate the pressure and temperature sensor or ultrasonic transducer.

Cell body 52 is separated into an upper chamber 72 and a lower chamber 74 which are connected by a narrow flow path 76. The inside surfaces in the upper and lower chambers 72, 74 of cell body 52 are finished to the appropriate specifications for sealing with an elastomeric or other seal. The region of the cell body 52 around the narrow flow path 76 is profiled to house a special optic sensor 78, a combined, single density-viscosity sensor 80, and a charging port 82 which may have a zero dead volume charging valve 84 (See FIG. 2 and FIG. 3).

The zero dead volume charging valve 84 may have a variety of forms. Examples include valves available from CENERG-TEP laboratory of the ENSMP (Ecole Nationale Superieure des Mines de Paris). The charging valve 84 can also be constructed to function as a sampling valve. In the embodiment illustrated, the flow path 76 can be of round, rectangular, or square cross-section, and is designed specifically for the efficient and proper operation of the optic sensor 78 and the density-viscosity sensor 80. The surface finish of this narrow path may be smooth or specially designed to optimize the performance of the optic sensor 78 and density-viscosity (DV) sensor 80. The charging port 82 may be machined or otherwise formed into the cell body 52 for the purpose of charging and discharging cell contents.

The agitator mechanism 66, e.g. ultrasonic transducer, is used to agitate the sample to both decrease the time for equilibrium during phase separation and to quickly recombine the sample from two phases, gas and liquid, to a single phase homogenous mixture. The principle of ultrasonic stirring, used in the chemical industry and in various laboratory equipment, is employed to ensure equilibrium by causing circulation within the cell so that the gas and liquid phases in the cell are continuously contacted to ensure that mass diffusion is maximized, hence decreasing the time to equilibrium phase separation or recombination to a single phase homogenous mixture. In this application the transducer is under extreme pressures and temperatures and is therefore purpose-built and optimized for this testing and measurement application. The power, frequency, and duty cycle may also be optimized for the application and the different types of fluids studied. This implies that, depending on the fluid, a different power, frequency, and duty cycle may be used.

The integrated pressure and temperature sensor 64 may be in the form of a modified gauge for use in downhole applications such as a quartz, micro-sapphire or SOI (silicon on insulator) type. The temperature portion of the sensor 64 may be a highly accurate RTD (Resistance Temperature Detector) type or equivalent. Components 64 and 66 are purpose built integrated designs which may be coupled to or integrally formed with the upper and lower pistons 68, 70, respectively, in cell body 52. In the example illustrated, the pressure and temperature sensor 64 and the ultrasonic transducer 66 are not placed into any recess of the piston structure; instead they form the piston in a one component integrated design.

The gauge housing is specifically machined for the purpose of integrating all these functions into a single one piece design. The wetted components of sensor 64/transducer 66 which are exposed to pressure and temperature are hermetically sealed. Additionally, sealing grooves 86 are used to seal components 64, 66 onto the cell body 52 using an elastomeric seal or other suitable seal. The dual function sensor and piston (e.g. sensor 64/piston 68 and transducer 66/piston 70) enables a smaller cell design which minimizes overall cell volume, cell dead volume, and hence thermal mass of the cell. In the example illustrated, the pressure and temperature sensor 64 serves as the top piston to minimize the amount of sealing interfaces. Dead volume reduction is desirable because dead volumes can affect experimental accuracy and/or measurement resolution.

Extended housing portions 60 and 62 may serve as conduits for the electrical connections to the respective sensor 64 and ultrasonic transducer 66. The exposed ends 88, 90 of the extended housings 60, 62 may be sealed by a bulkhead or sealed by other means to prevent any ingress. The extended housing portion 62 may be secured to a base plate 92 of the modular sensor assembly 50 by a fastener 94. Similarly, extended housing portion 60 may be secured to a piston guide plate 96 by a fastener 98. There is no pressure on ends 88 and 90. Electrical connections to auxiliary equipment used for operations involving components 64 and 66 may be made through exposed ends 88 and 90. Additionally, sealing grooves and corresponding seals 100 are used to seal extended housings 60, 62 with respect to the corresponding end caps 58. The seals may comprise elastomeric seals or other suitable seals.

Figure 2:
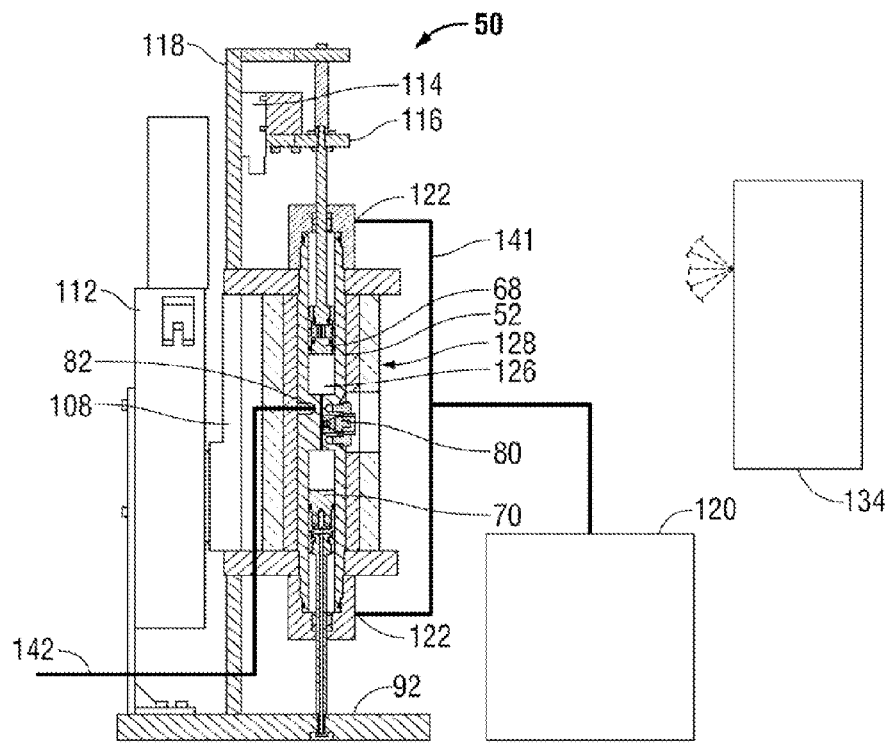
FIG. 2 is a schematic illustration of the modular sensor assembly with supporting components, according to an embodiment of the present invention.
Figure 3:
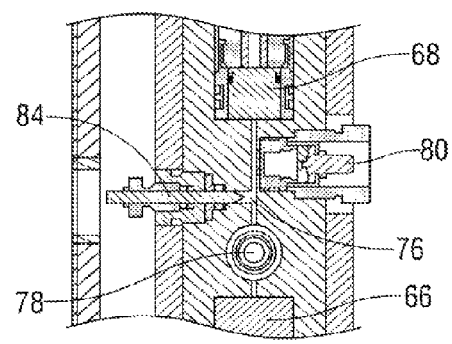
FIG. 3 is a schematic illustration of a portion of the modular sensor assembly, according to an embodiment of the present invention.
Figure 4:
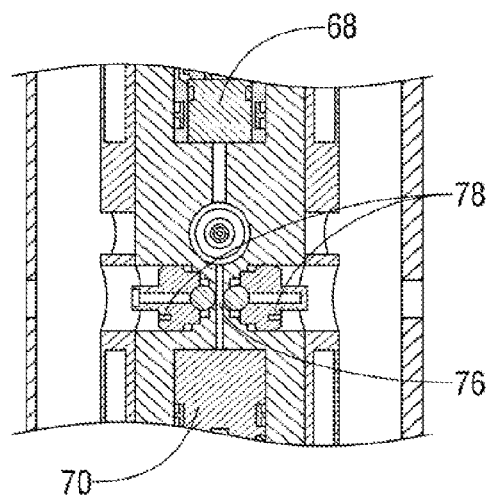
FIG. 4 is another schematic illustration of a portion of the modular sensor assembly, according to an embodiment of the present invention.

In the embodiment illustrated, the cell body 52 is held by a frame which may comprise base plate 92, a plurality of guide rods 102, a top plate 104, cell guide plates 106, and a cell mounting bracket 108 (see FIG. 2). The cell body 52 is attached to cell mounting bracket 108 and allowed to slide up and down along the guide rods 102 through linear bearings 110. The combination ultrasonic transducer 66/lower piston 70 is held fixed relative to the frame by the base plate 92. As illustrated in FIG. 2, a high precision linear actuator 112 may be attached to the base plate 92 by a bracket to move the cell body 52 along the guide rods 102. The frame is constructed of high strength to weight material or other light weight materials to minimize overall weight. The linear actuator 112 may be a commercially available unit or equivalent with, for example, micrometer resolution and accuracy.

In this particular embodiment, a linear encoder sensor head 114 may be coupled to the combination pressure and temperature sensor 64/upper piston 68 by a connecting bracket 116 and to a magnetic strip encoder 118 which also may be attached to the frame. The encoder sensor head 114 and magnetic strip encoder 118 may be designed or selected with micrometer resolution and accuracy to track the position of upper piston 68 which is allowed to move within cell body 52. An air actuated rod lock can be attached to piston guide plate 96 and can clamp to the guide rods 102 to hold upper piston 68 fixed during motion of cell body 52. The cell body 52 and upper pressure/temperature sensor 64/piston 68 are moved independently. By way of example, piston 68 may be moved by regulating hydraulic fluid pressure/flow with a hydraulic pump 120. Hydraulic pump 120 is used to deliver pressurized hydraulic fluid to ports 122 which extend through end caps 58 and deliver the fluid to hydraulic chambers 124 to selectively move the desired piston or pistons. By way of example, the hydraulic pump 120 may be a commercially available dual piston displacement type pump with non-pulsating continuous flow or equivalent. The ports 122 may be profiled for commercially available high pressure fittings or equivalent.

The sealing configuration provided by sealing grooves and corresponding seals 54, 86, and 100 further subdivides the interior chamber of the cell body 52 into the upper chamber 72 and the lower chamber 74. The upper chamber 72 and lower chamber 74 have a "hydraulic side" with hydraulic fluid in hydraulic fluid chambers 124 and a "sample side" with a fluid sample in a sample chamber 126 comprising portions of upper chamber 72 and lower chamber 74. The sample side is formed between the upper piston 68 and the lower piston 70 on either side of the narrow channel or flow path 76. The hydraulic fluid on the hydraulic sides minimizes the differential pressure across the sealing groove 86, hence reducing the tendency for a leak across the seals. This allows operation at very high pressures and temperatures. The lower end cap 58 may also have a port 122 for hydraulic fluid. Hydraulic fluid on the lower end cap 58 serves to minimize differential pressure across the corresponding sealing groove 86 and also serves to reduce the differential pressure across the ultrasonic transducer 66. The volume of the sample on the sample side can be changed by moving the upper piston 68.

This configuration also ensures that the fluid sample in sample chamber 126 can contact the optic sensor 78 and single density-viscosity sensor 80 by moving the cell body 52 and hence the optic sensor 78 and density-viscosity sensor 80, through the sample fluid column. The liquid phase column height varies with gas solubility, which for a given fluid is dependent on pressure and temperature. Hence, by moving the cell body, the sensors can be located in the region of the fluid where the measurement needs to be made, for example gas-liquid interface, liquid phase density, and liquid phase viscosity. The relative position of the optic sensor 78 and the density-viscosity sensor 80 enables this process to be automated (See FIG. 2 and FIG. 3). Once the gas interface is detected, the cell body 52 can move some additional distance, e.g. at least the separation distance between the optic sensor 78 and the density-viscosity sensor 80, to position the density-viscosity sensor 80 in the liquid phase. This is useful for measuring liquid phase properties with fluids with different gas solubilities and will be explained in the subsequent discussion on the operation of the modular sensor assembly 50. The pressure of the sample fluid in sample chamber 126 is controlled by moving upper piston 68. When cell body 52 is in motion, upper piston 68 is held fixed to maintain sample pressure.

Cell body 52 may be heated to raise the sample temperature to reservoir temperature or to another desired temperature by a thermal management system 128. According to one embodiment, the thermal management system 128 comprises an inner shell 130 which may be controlled to provide both heating and cooling. The inner shell 130 is designed so that it closely fits the geometry of the cell body 52 to maximize thermal contact and maximize heat transfer to the cell body 52. Thermal management system 128 may also comprise an outer shell 132 in the form of an insulating layer designed to minimize heat loss or gain from the external environment. Thermal management system 128 forms a lightweight encapsulating thermal boundary capable of maintaining system temperature within a desired range, e.g. <±0.5° C., and to minimize thermal gradients along the length of cell body 52. Heating is achieved by electric resistance or by other suitable heating mechanisms, and the cooling can be achieved by air circulation, or water circulation within encapsulating inner shell 130. When the temperature of the system is lower than the ambient temperature, a suitable heat transfer fluid that circulates through an external refrigeration or similar system may be employed. The outer shell 132 of the thermal management system 128 maintains a suitable external touch temperature for operator safety.

Thermal management system 128 is controlled and monitored by a processor-based control system 134, e.g. a microcomputer system, or other suitable control system. The control system 134 may be used to automate the sampling procedure by also controlling movement of pistons, e.g. movement of upper piston 68, and by obtaining data from the density-viscosity sensor 80, pressure and temperature sensor 64, optic sensor 78, and/or other system sensors. The control system 134 may also be used to control charging and removal of the fluid sample with respect to fluid sample chamber 126, along with controlling other components and functions of the overall testing and measurement process.

Figure 5:
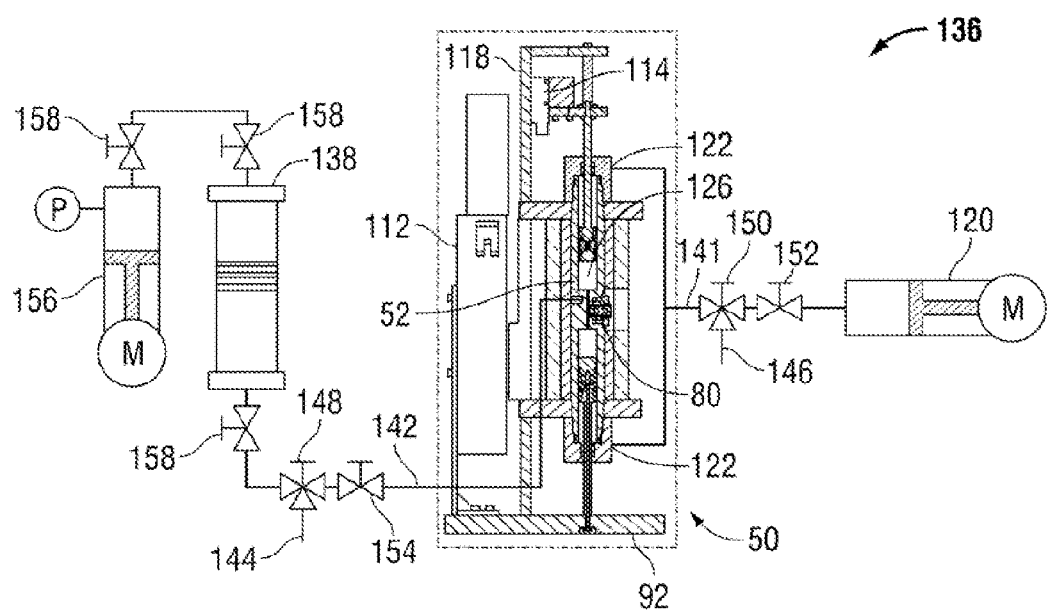
FIG. 5 is a schematic illustration demonstrating operation of the modular sensor assembly, according to an embodiment of the present invention.
Figure 6:
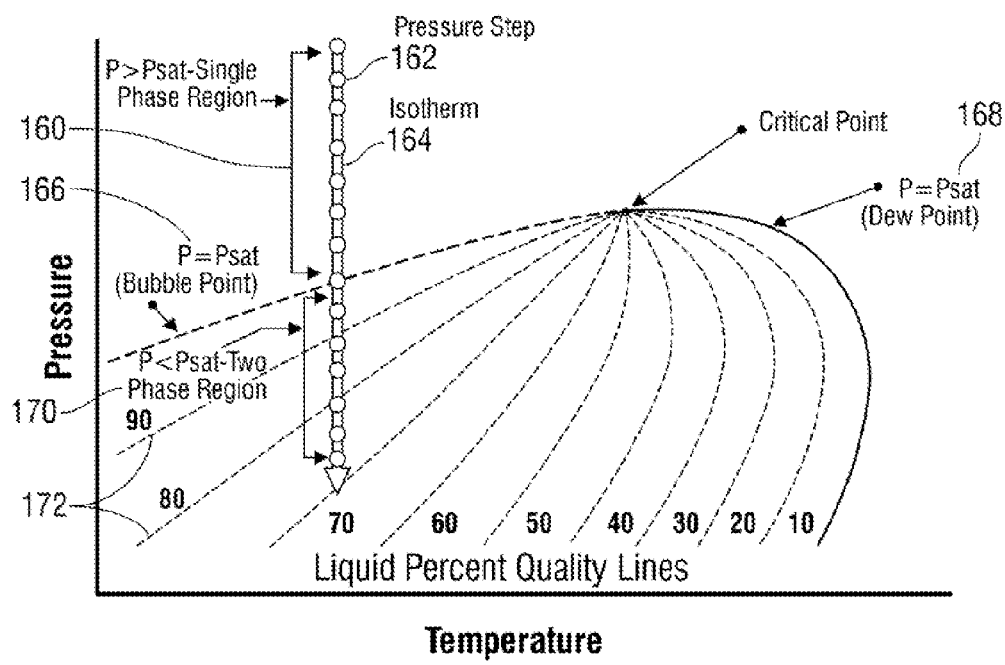
FIG. 6 is a graph showing a generalized phase envelope for a reservoir fluid plotting pressure versus temperature.

Referring generally to FIGS. 5 and 6, one example of the general operation of modular sensor assembly 50 is illustrated. It should be noted that modular sensor assembly 50 may be operated in conjunction with other modules that perform other tests to, for example, ensure that the results obtained from modular sensor assembly 50 and the overall sensor system 136 are of the desired quality.

As illustrated in FIG. 6, a generalized phase envelope for a reservoir fluid is employed to illustrate how measurements are made during a typical experimental run. The basic steps of a Constant Composition Expansion (CCE) experiment will be used in the subsequent discussion to explain the operation of the system 136. The system 136 may be used for other experiments such as Constant Volume Depletion tests, Separator tests, and Differential Liberation tests. In this example, the measurements to be made during a CCE experiment at each pressure step (at constant temperature) are as follows: Single Phase Volume and Total Sample Volume, Single Phase Density, Single Phase Viscosity, Liquid and Gas Phase Volumes (by measuring the gas-liquid interface), Coexisting Equilibrium Liquid Phase Density and Viscosity. The saturation pressure can also be detected by determining the pressure at which a second fluid phase forms.

Prior to performing an experiment with system 136, the sample is prepared in a sample cylinder 138 of the overall system 136 (see FIG. 5). It is assumed that the system 136 has been thoroughly cleaned, all calibrations on the sensors and the system have been verified, and the system has been pressure tested. The fluid sample in cylinder 138 may be obtained from a downhole sampling tool or from a recombined surface wellhead separator, e.g. see FIG. 13. In the case of the downhole fluid sample, it is assumed that the sample transfer from the tool to the sample cylinder 138 has been validated and the sample is free of contaminants, e.g. sand and mud, and is within specifications for water content. For the surface sample case, it is assumed that the sample has been recombined from separator liquid and gas phase samples and that the recombined sample has been validated and is representative of the reservoir fluid to be studied. Further, it is assumed that, in either case, the sample has been transferred into the sample cylinder 138, and the fluid in sample cylinder 138 has been restored to a monophasic homogenous composition at the reservoir pressure and temperature or other desired pressure and temperature.

In this operational example, cell body 52 is moved by linear actuator 112 along guide rods 102 through linear bearings 110 attached to cell guide plate 106 so that lower piston 70 is at its uppermost position in lower chamber 74. Upper piston 68 is moved to the lowermost position in the upper chamber 72 by varying the pressure or volume of the hydraulic fluid on the hydraulic side of upper chamber 72 via hydraulic pump 120. Upper piston 68 is guided as guide bushings 140 and piston guide plate 96 move relative to guide rods 102 (see FIG. 1). Prior to sample transfer into cell body 52, the volume of sample in chamber 126 between the upper piston 68 and the lower piston 70 is made as small as possible, which is desirable as described in greater detail below.

The modular sensor assembly 50 is evacuated by a vacuum pump to remove air and other contaminants from the hydraulic sides and sample sides of upper and lower chambers 72, 74 and from the transfer lines 141 and 142. Air is considered a sample contaminant and entrapped air can affect pressure measurements and system performance due to its compressibility and solubility in the liquid phase. Evacuation is done through vacuum pump lines 144 and 146 which are connected to a vacuum pump through three-way valves 148 and 150, respectively. The three-way valves 148 and 150 are also connected to the sample and hydraulic sides of the sample chamber 126 comprising upper chamber 72 and lower chamber 74. This arrangement ensures that all air is evacuated not only from the chambers 72, 74 but also from all the connecting transfer lines 141, 142. Hydraulic fluid is charged in through port 122 from hydraulic pump 120 via high pressure tubing transfer line 141 until the hydraulic sides of chambers 72, 74 are full of hydraulic fluid. The cell body 52 is then heated to reservoir temperature or other desired temperature by the thermal management system 128. Additionally, transfer line 142 may be heat traced to prevent any cooling that could cause dropout of heavy end fluid components or wax formation during transfer of the fluid sample from cylinder 138 to the sample chamber 126. This ensures a representative sample is transferred. A valve 152 (it is assumed that the hydraulic fluid is present on the pump end) is shut and a valve 154 is opened as illustrated.

Once the system pistons 68, 70 have been positioned as described above, the system has been evacuated of air, and the temperature has been stabilized, the sample transfer is completed by displacing a fluid sample from the sample cylinder 138 using a pump 156 (or pump 120 may be configured to perform this function as well) and flow may be conducted through one or more valves 158 before reaching three-way valve 148. The fluid sample is further displaced through high pressure corrosion resistant transfer line 142 into sample chamber 126. Valve 152 is opened and three-way valves 148, 150 are suitably positioned. The linear encoder 114 can be zeroed or the current reading can be used as the reference. It is assumed that the system dead volumes due to the transfer lines, valves, and fittings have been taken into account in the calibration procedure.

The transfer takes place as close to isobaric conditions as possible. Initially, because of the aforementioned dead volumes and the minimal volume of the sample chamber 126 in the cell body 52 the sample will flash, that is, it will go from being monophasic and homogenous to a multiphase non-homogeneous fluid. Hence, by minimizing the dead volume and volume of sample chamber 126, this undesirable effect is kept to a minimum—the smaller the volume the faster the pressure recovery. The ultrasonic agitator 66 may be started to recombine the fluid to a single phase homogenous fluid at this initial stage in the charging process. Once the fluid is single phase and homogeneous, and the pressure recovery and near isobaric transfer are completed, the ultrasonic agitator 66 is run, according to a predefined duty cycle, throughout the transfer to ensure homogeneity. The amount of sample charged will depend on the fluid type (fluids ranging from natural gases to heavy oils) and the experimental parameters, such as the final pressure of the CCE. The volume charged into the sample chamber 126 is recorded by the change in displacement of the upper piston 68 along the magnetic strip encoder 118 via encoder head 114 attached to the extended housing portion 60. The final volume is only read once the system has stabilized, i.e. when temperature and pressure remain constant and the other sensors report constant values. A calibration factor for the cell geometry is used to convert the linear encoder displacement to volume which is then corrected for the dead volumes of the transfer line valve and fittings. Once completed, valve 154 is shut so the sample is isolated within the cell body 52.

After the isolated sample in cell body 52 has stabilized, i.e. the sample has become a homogenous single phase mixture at constant temperature and pressure at the predefined starting conditions, the testing can proceed. This starting point is usually in the illustrated region 160 in FIG. 6, well above the saturation pressure locus which is the so called single phase region.

Prior to the start of testing, a plan may be developed to select a predetermined start temperature and pressure, such as the reservoir pressure and temperature. Also from the pre-planning, a predetermined number of pressure steps 162 (this may be changed as the experiment is proceeding) are selected along the starting isotherm 164 and a preliminary estimate of the saturation pressure (166 or 168) may be available from EOS predictions based on available single stage flash experimental and or other PVT data. At each pressure step above, 160, and below, 170, the saturation point (166 or 168), volume (total volume and phase volumes (P<Psat)), density, and viscosity measurements can be made. The pressure steps well above the saturation pressure, i.e. at region 160, are generally coarse with a finer interval being used around the saturation pressure and then a coarse interval in the two phase region, 170. A finer interval can be used throughout if desired. Around the saturation pressure, the system may be held for a period at constant pressure to allow sufficient time for the liquid and gas phases to equilibrate. This prevents the false detection of saturation pressure due to the formation of metastable states. The agitation system 66 may be left on for certain measurements like saturation pressure but turned off for volume and density/viscosity measurements. The saturation pressure 166, 168 is an important measurement and the testing may be performed initially with coarse pressure step intervals and, once an estimate of the saturation pressure is obtained, the pressure intervals can be made finer to increase the accuracy of this measurement. Generally, a preliminary run is made with the pre-planned steps. Once a rough estimate of saturation pressure is obtained, the fluid is recombined back into a single phase homogenous mixture and the pressure steps around the estimated saturation pressure can be made finer if required for the re-run. This pressurization and depressurization around the saturation pressure 166, 168 can be repeated several times.

The cell body 52 is held fixed and the upper piston 68 is used to control the pressure of the fluid as previously described. The upper piston 68, from its starting pressure (the equipment is assumed to be at the starting temperature) isothermally expands the fluid. The ultrasonic agitator 66, during the expansion, is operated in a manner so as not to heat the fluid contained in sample chamber 126, e.g. operated in a pulsed mode. At various predefined pressure steps the upper piston 68 is stopped and the fluid sample in sample chamber 126 is allowed to stabilize before any measurements are made, that is, come to a constant pressure and temperature (the fluid sample temperature may change slightly due to expansion, hence a small amount of time is required to re-establish temperature equilibrium—a constant volume indicates stability).

Certain single phase measurements, in region 160, can be made as functions of pressure and temperature at the various single phase pressure steps and include: total volume (measure of compressibility), single phase density, and single phase viscosity. The first measurement is made at the starting conditions with subsequent measurements being made at the predefined steps. Because the fluid is single phase and homogeneous, there is no need to move the optic sensor 78 and the density-viscosity sensors 80 attached to cell body 52. The ultrasonic transducer 66 is operated, according to a predefined duty cycle, to ensure homogeneity. The cell body 52 can be moved to position the optic sensor 78 and density-viscosity sensor 80, both fixed to cell body 52, at a different position in the fluid sample to make additional measurements at different locations in the fluid to confirm homogeneity. The upper piston 68 may be moved during this process if required. In the example illustrated, the upper piston 68 is automatically controlled by control system 134 to ensure the sample is maintained at isobaric conditions or close to isobaric conditions. The measurements are only made once the fluid has stabilized. The upper piston 68 controls the fluid pressure and the cell body 52 controls the position of the sensors 78, 80 relative to the fluid sample contained in sample chamber 126. The movement of the cell body 52 has been described previously, and the single phase volume may be measured using linear encoder 114. The optic sensor 78 can be used at this stage to verify that the sample is single phase and homogeneous.

Figure 7:
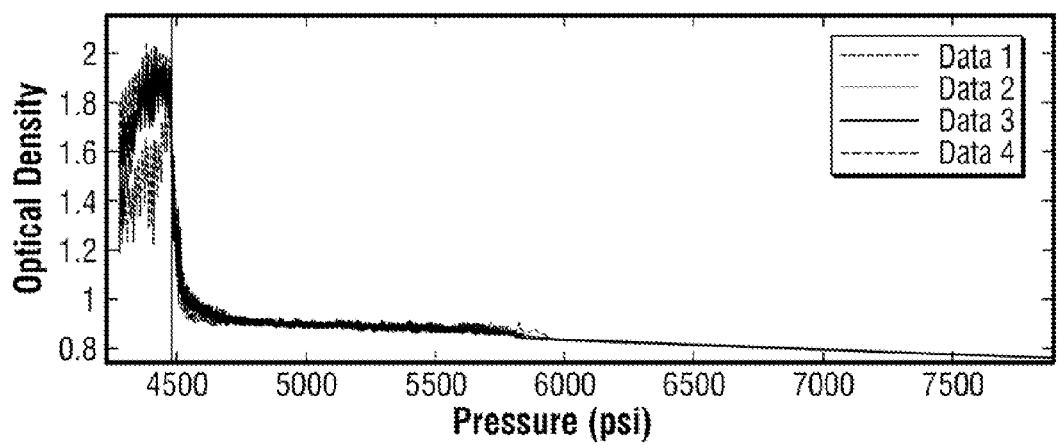
FIG. 7 is a graph showing a spectral response of a fluid sample using an optic sensor.

The expansion of the fluid continues until the saturation point on the phase envelope is reached, and a bubble point or dew point measurement is made depending on fluid type. The saturation point is detected by the optic sensor 78 which uses spectroscopic techniques to monitor changes in the fluid properties such as optical density. According to one embodiment, the optic sensor 78 comprises two small diameter sapphire balls placed directly opposite (mirror image) each other across narrow flow path 76 to serve as lenses mounted in the narrow flow path 76. Narrow flow path 76 also functions as the optic path and provides the means, via its reduced size, to measure through completely opaque dark hydrocarbons. The small diameter sapphire ball lenses are easy to seal and provide very good high pressure resistance as compared to flat windows. The twin set of lenses relay a small point of light to a small detector or fiber optic (less than 300 microns in diameter). The lenses function to provide a collimated light path in the interrogation volume and, by focusing the output light onto a small fiber or detector, greatly enhance bubble, dew, and gas-liquid interface detection. Through custom fittings, two fibre optic cables are connected through a light source and spectrometer or other such device. The sensor is directly incorporated in the apparatus and hence reduces dead volume and facilitates in-situ measurements of the saturation pressure. The spectrum is recorded during the testing. Spectral optical density changes as a function of pressure, at a given temperature, and there is a gradual change in optical density as the fluid is expanded. At the saturation point, a noticeable step change in the spectral response occurs, e.g. microbubbles/microdroplets are formed in the fluid, and indicates the onset of the bubble/dew point. Because optical density and spectra are made via transmission, and not refraction/reflection surface detection, the sensor does not require the droplet to be deposited on the lens, but can occur anywhere in the interrogation volume. This sensitive step change in optical density is correlated to the saturation pressure (indicated by the knee point in FIG. 7) in conjunction with the pressure sensor 64 and volume measurement obtained from the linear encoder 114 (this allows calculation of a pressure versus volume curve on lower gas-oil ratio (GOR) oils via system software using the data and signal flow of FIG. 14). For the preliminary estimation of the bubble point, the modular sensor assembly 50 can be depressurized continuously at a predetermined rate to arrive at a coarse estimate.

As stated earlier, the fluid can be recombined by the ultrasonic agitator 66 and by increasing pressure above the saturation pressure. The testing pressure steps can be refined to decrease the uncertainty of the saturation pressure or to confirm the saturation pressure.

Below the saturation pressure point (two phase region 170), measurements may be made as functions of pressure and temperature and include; total volume, phase volumes (liquid and gas phases), liquid phase density, liquid phase viscosity, gas phase density, and gas phase viscosity. The volume measurements, at saturation and liquid phase volumes, can be used for determining the quality lines 172 (percent liquid) of the phase envelope to completely characterize the reservoir fluid phase behavior at that temperature. The agitator 66 may be run according to a predetermined duty cycle as described earlier to speed up the equilibrium process.

Figure 8:
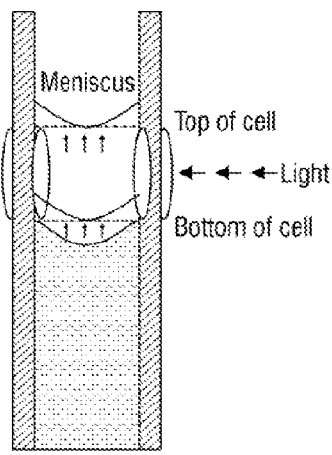
FIG. 8 is a schematic illustration of the optic sensor showing detection of a gas-liquid interface.
Figure 9:
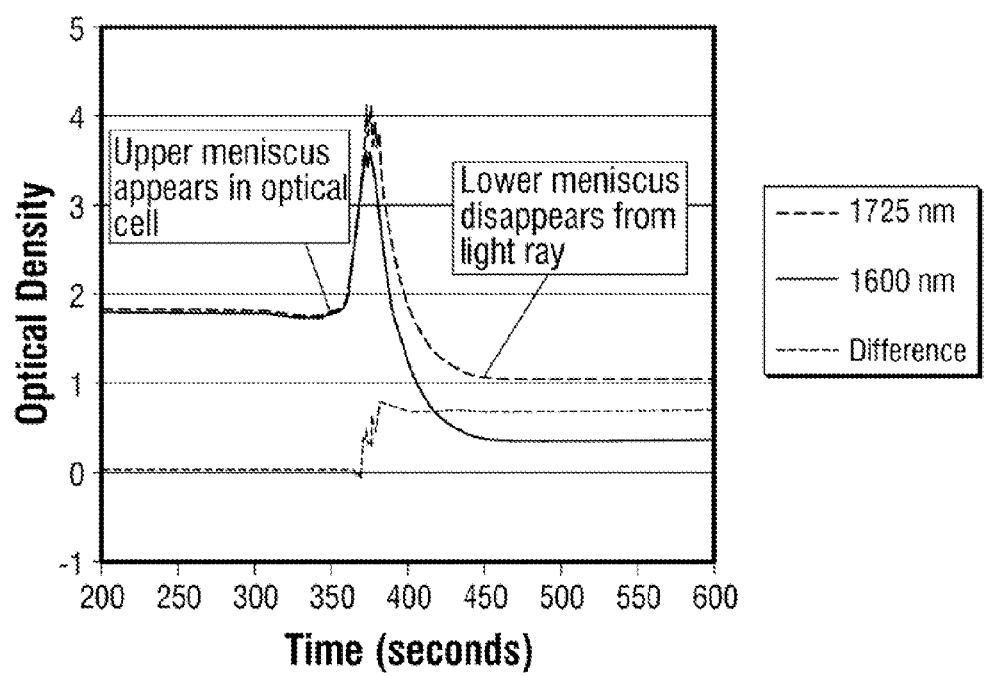
FIG. 9 is a graph showing a spectral response from the optic sensor of FIG. 8 illustrating the detection of a gas-liquid interface for a fluid sample.
Figure 10:
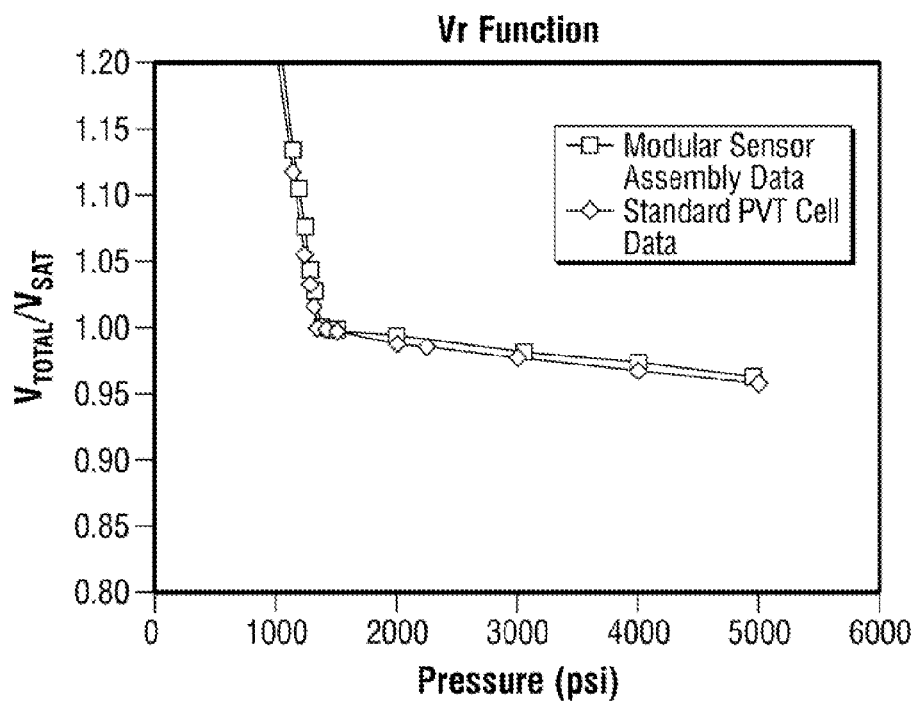
FIG. 10 is a graph showing relative volume curves of a fluid sample.
Figure 11:
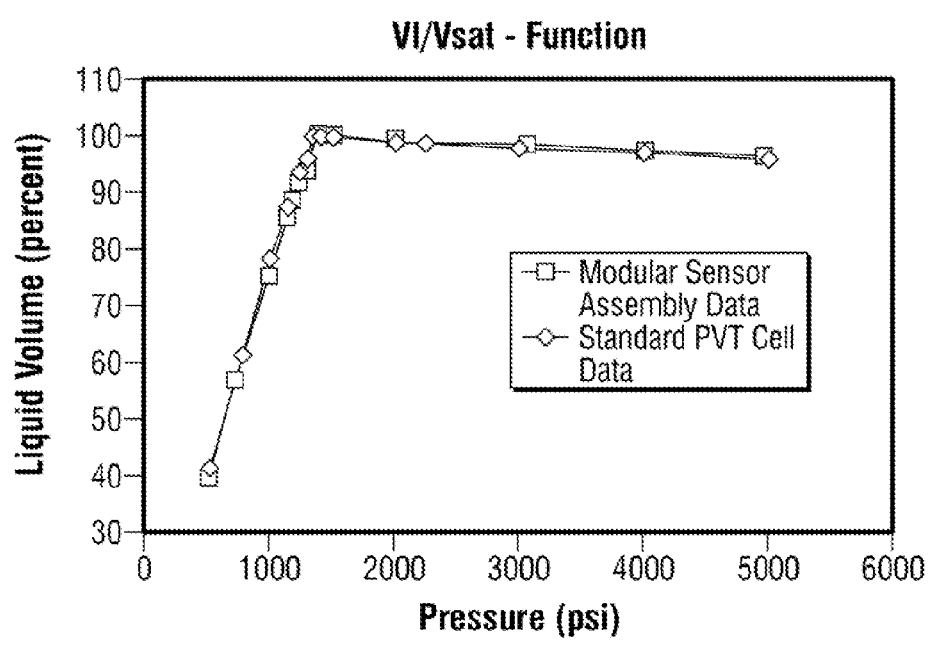
FIG. 11 is a graph showing liquid phase volume/saturation volume curves of a fluid sample.

In this embodiment, the optic sensor 78 also detects the gas-liquid interface, as illustrated by the examples provided in FIGS. 8 and 9. (FIG. 8 illustrates optic sensor 78 used to detect the gas-liquid interface of a fluid; and FIG. 9 graphically illustrates a spectral response using optic sensor 78 to show detection of a gas-liquid interface for a hydrocarbon liquid-air interface). The optic sensor 78 minimizes dead volume and is customized for this application and geometry of cell body 52. By way of example, the optic sensor 78 may be that described in US Patent Application Publication 2010/0265492. By knowing the total sample volume (from the linear encoder 114) and the position of the phase interface using optic sensor 78 and the linear actuator 112, the volumes of the gas and liquid phases respectively can be measured, as indicated by the examples provided in the graphs of FIG. 10 and FIG. 11. (FIG. 10 graphically illustrates a relative volume curve generated by the modular sensor assembly 50 compared to data generated by a standard PVT cell; and FIG. 11 graphically illustrates a liquid phase volume/saturation volume curve generated by the modular sensor assembly 50 compared to data generated by a standard PVT cell.) Because of the near-infrared spectroscopy detection of the meniscus (where oil has a low optical density), the lower and upper meniscus is easily detected even in very dark opaque hydrocarbons. Spectroscopic detection at two or more wavelengths allows for the determination of pure gas and pure hydrocarbon regions, as well as discrimination of oil from water menisci.

The phase densities and viscosities provide additional data which can be used to enhance the results of the sample tests. The present invention provides the ability to measure the liquid phase densities (and gas phase densities) without the need to transfer to another measuring device, either external or internal. By incorporating the micro density-viscosity sensor 80 in the apparatus (in narrow flow path 76) it is in contact with the fluid sample in sample chamber 126. By moving the cell body 52, to which the sensor 80 is attached, the measurements of the phase densities and viscosities are achieved.

Once the location of the gas-liquid interface is known, combined with knowledge of the relative distance between the optic sensor 78 and the density-viscosity sensor 80, the liquid phase density and viscosity can be measured. This measurement is achieved by moving the cell body 52 as previously described.

By way of example, the density-viscosity sensor 80 may be a flush mounted sensor selected and customized for a specific application and cell geometry of cell body 52. This sensor may be a modified version of that described in US Patent Application Publications 2008/0156093 and 2008/0257036. The density-viscosity sensor 80 located in narrow flow path 76 is in direct contact with the fluid sample in sample chamber 126 and protected from damage from upper and lower pistons 68 and 70. Gas viscosity is normally calculated and gas density is normally measured gravimetrically, which requires sampling that can result in experimental errors. As shown in another embodiment described below, these gas phase measurements may be directly measured without the need for sampling.

Ultrasonic transducer 66 and/or cell body 52 may be designed to avoid extraneous resonant modes and with a custom power supply to maximize acoustic energy transfer to the fluid with varying cell geometry due to the movement of piston and/or cell body. In the embodiment illustrated, ultrasonic transducer 66 is designed with sufficient bandwidth to allow for frequency modulation, which will therefore avoid standing waves. The geometry of cell body 52 may be optimized to ensure maximum energy transfer from ultrasonic transducer 66. Ultrasonic transducer 66 may also be optimized for the fluid type under study and for performance degradation due to the effect of pressure and temperature. Ultrasonic transducer 66 is designed to minimize coupling to cell body 52. The frequency of ultrasonic transducer 66 may be further optimized to gain the benefits of both cavitation and acoustic streaming Ultrasonic transducer 66 and its corresponding resonator/probe may be a single integrated design, or the transducer can be moved away from the cell body 52 and coupled to the resonator/probe via a waveguide, although the latter configuration will increase the overall length. Additionally, the resonator/probe can be a flat type, tapered type, or a cup-horn type. In the latter two instances the geometry of cell body 52 may be complementary.

Figure 12:
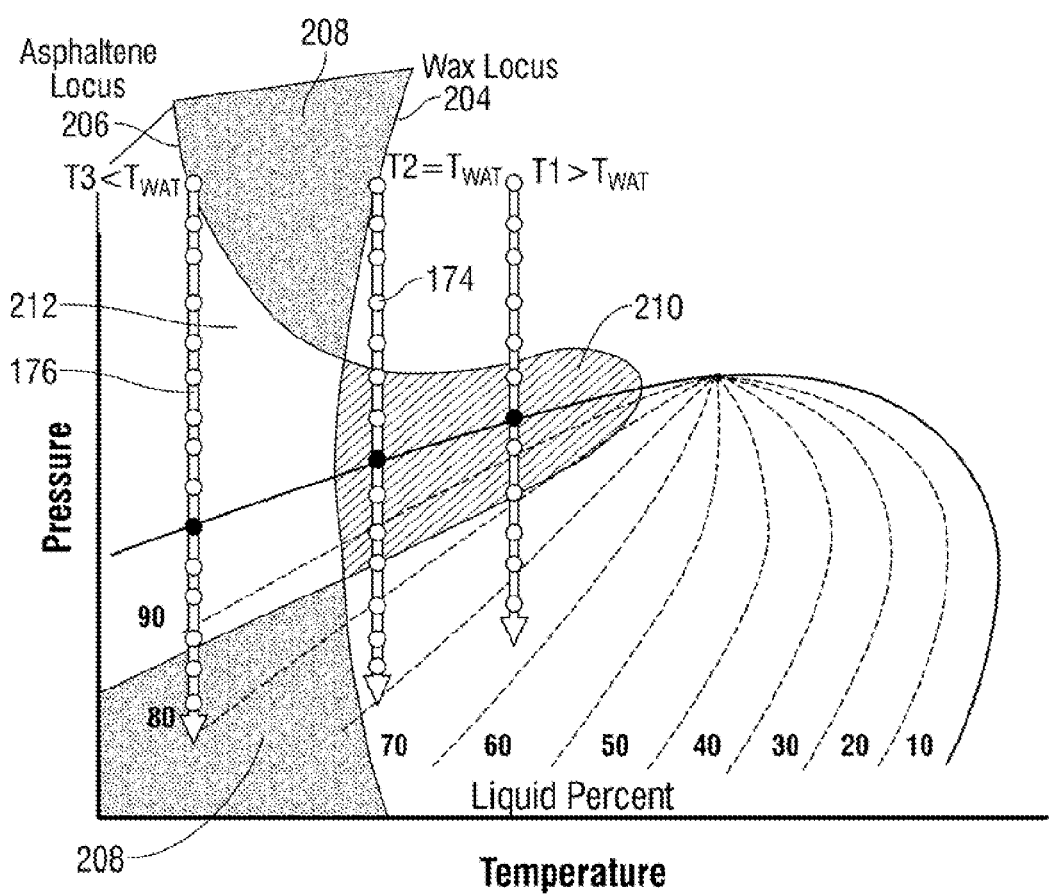
FIG. 12 is another example of a fluid phase envelope plotting pressure versus temperature.

In this example, the testing is carried out to completion at a predetermined stopping pressure or by maximizing the expansion volume available in the sample chamber 126. The modular sensor assembly 50 has the ability to heat and cool, hence the fluid can be recombined and the experiment can be repeated at different temperatures, as indicated by the different temperatures 174 and 176 shown on the temperature-pressure graph of FIG. 12. This will generate additional CCE data which includes additional density and viscosity data and, combined with Single Stage Flash and Composition data (see FIG. 13), is very beneficial in the development of equation of state (EOS) models to represent the reservoir fluid throughout the production cycle. The data are used to enhance EOS model tuning and may reduce the need to perform other PVT experiments, such as Differential Liberation (DL), Constant Volume Depletion (CVD) and Separator Tests (ST). Reducing the amount of tests reduces the turnaround time for a standard PVT study and also consumes less sample volume, which is advantageous from an operational point of view. Also, Separator Tests, CVD and DL are known to be error prone. Density and viscosity are usually measured by separate specialized devices such as a vibrating tube apparatus (density) and a falling body apparatus (viscosity).

In a DL and/or ST study, the density of the co-existing liquid phase (liquid phase below the saturation pressure) is normally a calculated property (based on mass balances) and is not a measured property. The viscosity of the co-existing liquid phases is often measured in a separate experiment, with a separate charge of the fluid. The DL and/or ST study is replicated and the fluid is then charged into the viscometer. This process closely replicates the DL study, but the resulting liquid phases may not be identical to those in the original DL study due to the inherent procedural errors involved in the process. Direct measurement of the in-situ liquid phases would deliver a more representative density and viscosity value of the co-existing liquid phase and would be less error prone due to being a direct measurement rather than a separate measurement or a calculated value. Normally, the viscosity and the density of the co-existing phases produced during a condensate PVT study are not measured. The density in a CVD test, similar to the DL and ST, is determined mathematically. Acquisition of these direct measurements in a condensate system is novel and improves the data set used in EOS modelling of these systems The modular sensor assembly 50 can be operated in a variety of modes. For example, it can be operated in manual mode, semi-automatic (limited operator intervention), or fully automatic mode (no operator intervention once charged with the sample). The basic operation does not vary for each of these modes.

There are also several different methods that can be used to make certain measurements. Generally these can be divided into two categories: a continuous method or a step method. In the continuous method the system is depressurized very slowly and the sensors are programmed to make continuous measurements during the depressurization. Measurements such as saturation pressure, single phase densities, and single phase viscosities can be made. Single phase volume may be difficult to measure in this case. Although possible, the continuous method poses a number of challenges such as ensuring fluid equilibrium, ultrasonic transducer and stirring noise, and sensor acquisition rates. In some applications, this method may not be well suited for measurements such phase volumes, phase densities, and phase viscosities.

One method which works well is the step method as it overcomes the challenges of the continuous method and is regarded as more robust in obtaining accurate measurements. In the step method modular sensor assembly 50 makes important measurements at discrete times/steps (usually the pressure steps of interest) during the experiment where the noise effects of ultrasonic transducer 66 can be eliminated by shutting it off once fluid equilibrium is achieved. Although the sensors 64, 78, and 80 may be acquiring data continuously, the data required for the phase equilibrium calculations is extracted and averaged only at the discrete steps of interest. It is possible to operate modular sensor assembly 50 in both modes depending on the final objective. For example, with less accurate measurements the device can be operated using the continuous mode to obtain preliminary estimates in, for example, the determination of saturation pressure. The modular sensor assembly 50 and testing procedure may then be switched to step mode for making the accurate phase measurements. For some measurements, e.g. saturation pressure measurements, the noise effects of the ultrasonic transducer 66 can be compensated.

Modular sensor assembly 50 can be operated initially according to the continuous method to get an estimate of the saturation pressure. It can then be operated using the step method with finer steps around the saturation pressure. Alternatively, modular sensor assembly 50 can be operated in the step mode and once the saturation pressure is determined the fluids may be recombined and the steps refined around the saturation point. Effectively, modular sensor assembly 50 can be operated using a plurality of methods to make the measurements. The detailed discussion which follows illustrates only one possible method to help convey an understanding of the general operation of the modular sensor assembly 50 and overall sensor system 136.

Figure 13:
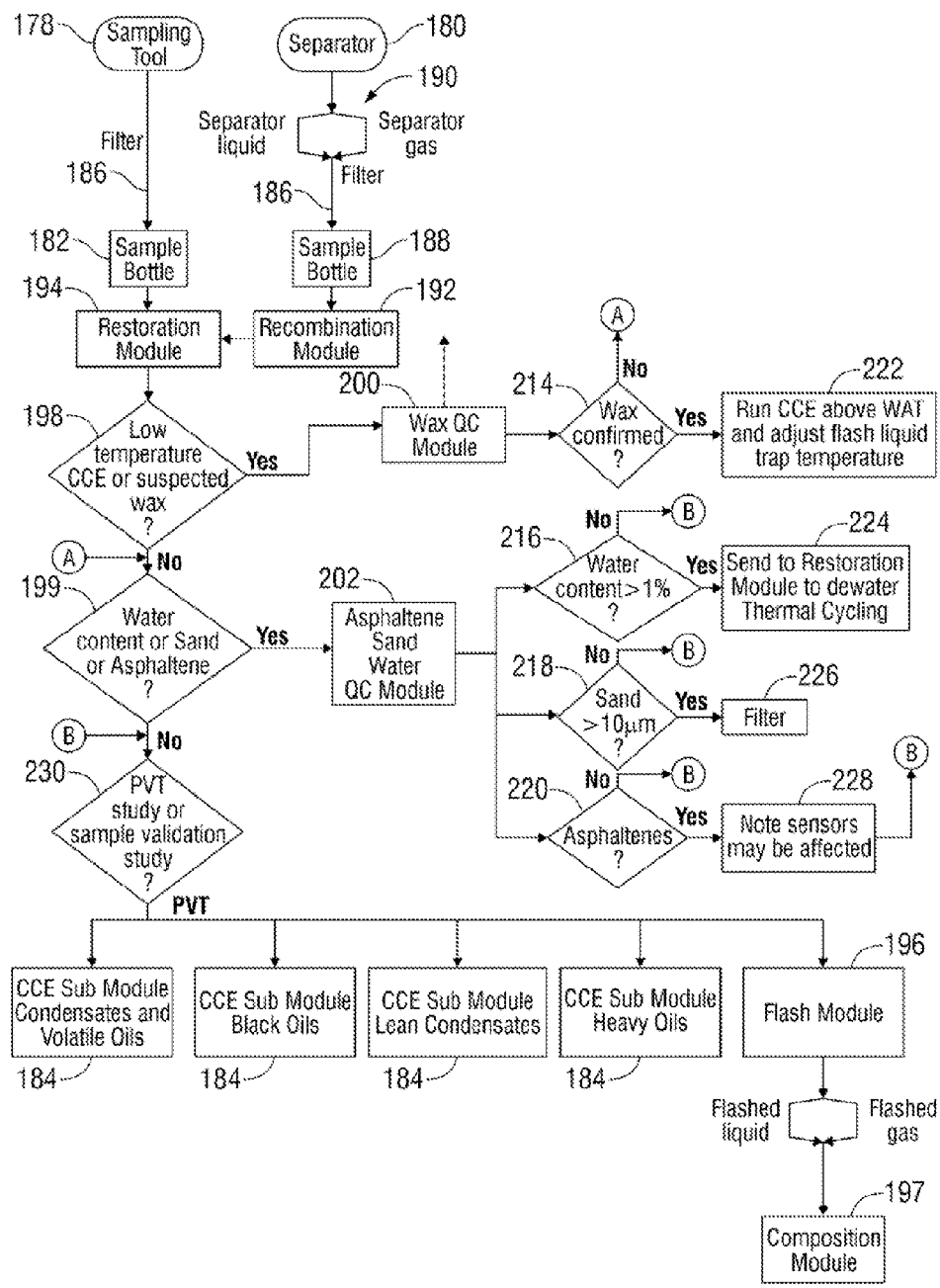
FIG. 13 is a schematic illustration showing a general workflow for processing a sample of a hydrocarbon-based fluid, according to an embodiment of the present invention.

Referring to FIG. 13, a generalized workflow and system description is provided with respect to utilizing modular sensor assembly 50 and overall sensor system 136. By way of example, fluid samples may be acquired from a downhole location 178, e.g. from a sampling tool, or from a surface location 180, e.g. from a surface separator.

In this example, downhole or surface samples can be checked by a transfer validation module 182, e.g. sample bottle, at every transfer in the process and additionally the samples can also be checked prior to charging sample into PVT modules 184. A high pressure filtration unit 186 may be placed either before or after the transfer validation module 182. Alternatively, or in addition, the sample may be transferred into a sample bottle 188 (in the case of separator samples) after separation of liquid and gas in a separator device 190.

In this example, the gas samples and liquid samples separated by separator device 190 are recombined to a single phase homogenous composition using a recombination module 192. Any sample bottle can be restored to the downhole reservoir pressure and temperature or any other condition by a restoration module 194. Recombined fluids require restoration and a validation check of composition via a sub sample sent to a flash module 196 and a composition module 197.

Further screening checks on restored and recombined samples are performed for wax precipitation onset (198) and for water content, solids contamination (e.g. sand), and asphaltene precipitation onset (199). In all cases quality control checks are performed by quality control (QC) modules 200 and 202, respectively. An important purpose for modules 200 and 202 is to ensure that the sample is acceptable for PVT or sample validation analysis and to detect any issues that can affect sensors in the modular sensor assembly 50, hence improving the quality of the analysis. Where multiple temperature runs are planned in modular sensor assembly 50, QC modules 200, 202 can be used to plan the experiment to avoid the wax and/or asphaltene loci 204, 206, respectively (see FIG. 12), or to confirm any anomaly in the experimental data points, e.g. wax and/or asphaltene deposition on sensors, that may affect the readings should these loci be crossed (wax precipitation in regions 208 and asphaltene precipitation in region 210 of FIG. 12). Further, QC modules 200 and 202 can provide additional data to estimate the asphaltene and wax loci 204, 206 and to determine the co-precipitation region (region 212 in FIG. 12) of the fluid under study. The optic sensor 78 may also be modified to perform these types of detection in sensor assembly 50 to, for example, provide information on live wax precipitation.

Confirmation of wax (see screening check 214), water (see screening check 216), sand (see screening check 218) or asphaltenes (see screening check 220) may result in the associated action represented by action blocks 222, 224, 226, and 228. Asphaltene and wax precipitation may affect sensor readings in modular sensor assembly 50 depending on severity.

Additionally, modular sensor assembly 50 may be configured specifically for the type of fluid under study. The sensor customizations are based on the various fluid types handled by PVT modules 184 if a PVT study is to be performed, as represented by screening check 230, on fluid samples including volatile oils, condensates, black oils, and heavy oils. Customizations can be made on the sensors, such as on the density-viscosity sensor 80. The range of density and viscosity is very wide between gas condensates and oils. To improve the accuracy of the density and viscosity measurements, for example, the density-viscosity sensor 80 may be customized for the range specific to the fluid type. For example, customization may be performed in certain sample testing because condensates in the gaseous state require a higher sensitivity version of the density-viscosity sensor 80 and heavy oils require a higher stiffness version. Further customization may be made to the cell body 52 and/or piston geometry of pistons 68, 70 to make the modular sensor assembly 50 more suited for measuring very low volumes of liquids (liquid dropout) of gas condensates using the standard industry technique of using conical pistons with complementary cell geometry.

The flash module 196 and the composition module 197 may be used to determine some of the measurements required in addition to those of modular sensor assembly 50 to complete a typical PVT study. For example, flash module 196 may provide gas and liquid samples for compositional analysis by the composition module 197. Regardless, modular sensor assembly 50 and its integrated sensors facilitate taking of the desired measurements without intervention of an operator. The automation of operator-dependent operations reduces experimental variability, hence improving repeatability and reproducibility of the experiments.

Figure 14:
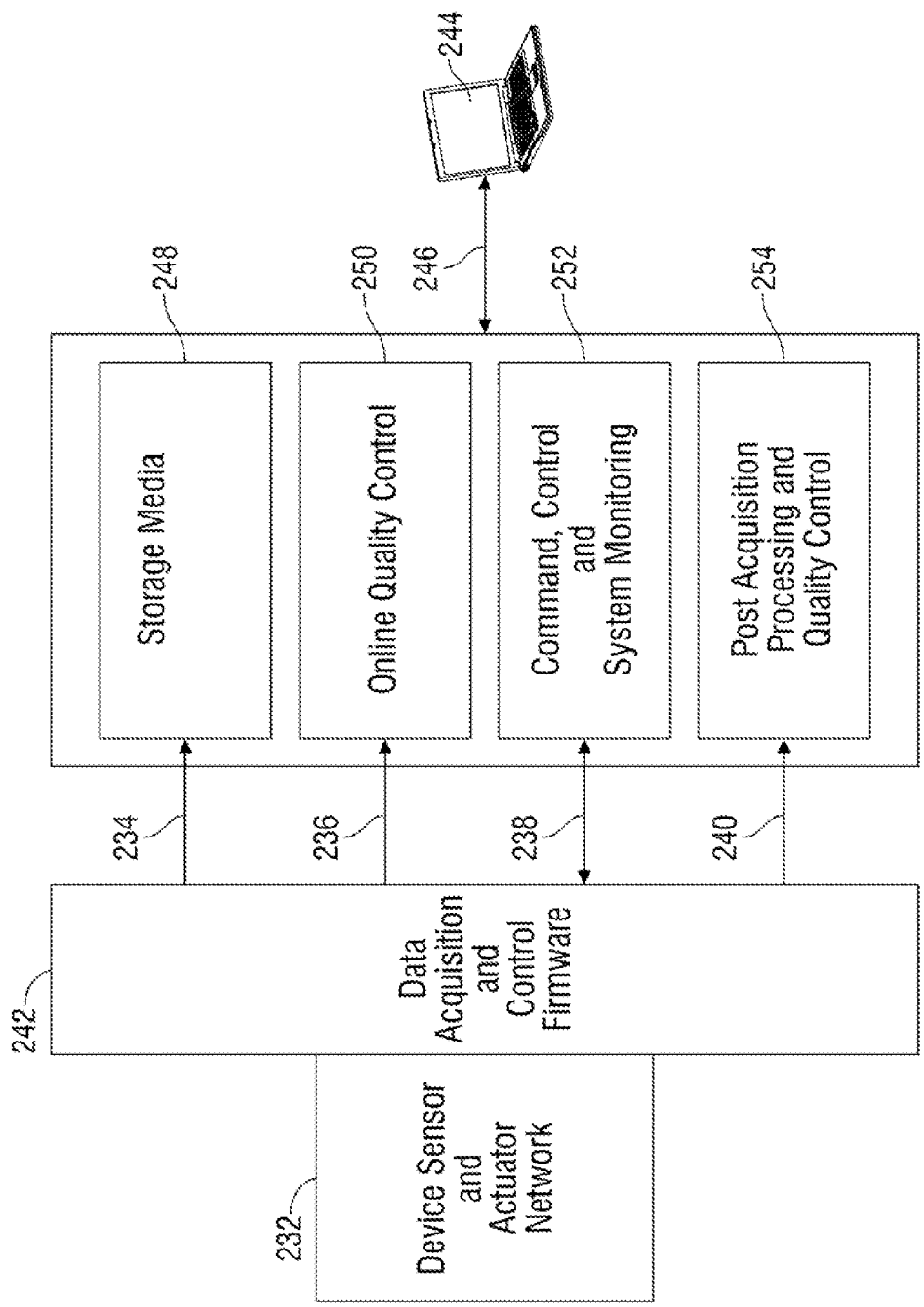
FIG. 14 is a schematic illustration showing a general data and signal flow during processing of a sample of a hydrocarbon-based fluid, according to an embodiment of the present invention.

As discussed above, the modular sensor assembly 50 and other components of the overall sensor system 136 may be controlled automatically via control system 134. Referring generally to FIG. 14, one embodiment of control system 134 is illustrated in a manner showing the general data and signal flow for controlling the sample test procedures. In this example, modular sensor assembly 50 has a local sensor and actuator network 232 which transmits data and control signals, represented by arrows 234, 236, 238, 240, via data acquisition and control firmware 242. The data and control signals are further transmitted to a processor system 244, e.g. a microcomputer, as represented by arrow 246. The processor system 244 may also be employed to log the transmitted data to some type of storage media 248 and to perform other tasks. For example, the processor system 244 may be employed to display the data to monitoring devices and to send data for online processing and quality control (time series analysis, threshold monitoring), as represented by block 250. Additionally, processor system 244 may be employed to send data to a microprocessor-based command and control system 252 which will then send correction signals to the actuators (see arrow 238) to maintain experimental conditions or to manipulate the device either in manual, semi-automatic, or automatic mode. The data may also be sent to an offline processing module 254 for post acquisition quality control and for further experimental data processing.

The design of modular sensor assembly 50 and associated components enables easy modification and adjustment of the components and configuration to readily facilitate testing of other types of fluids or other fluids according to alternate test procedures. Furthermore, the modularity of modular sensor assembly 50 enables addition, removal, and interchanging of components to facilitate various sampling and testing procedures. Several alternate embodiments and modifications of the modular sensor assembly 50 and overall sensor system 136 are discussed below.

Figure 15:
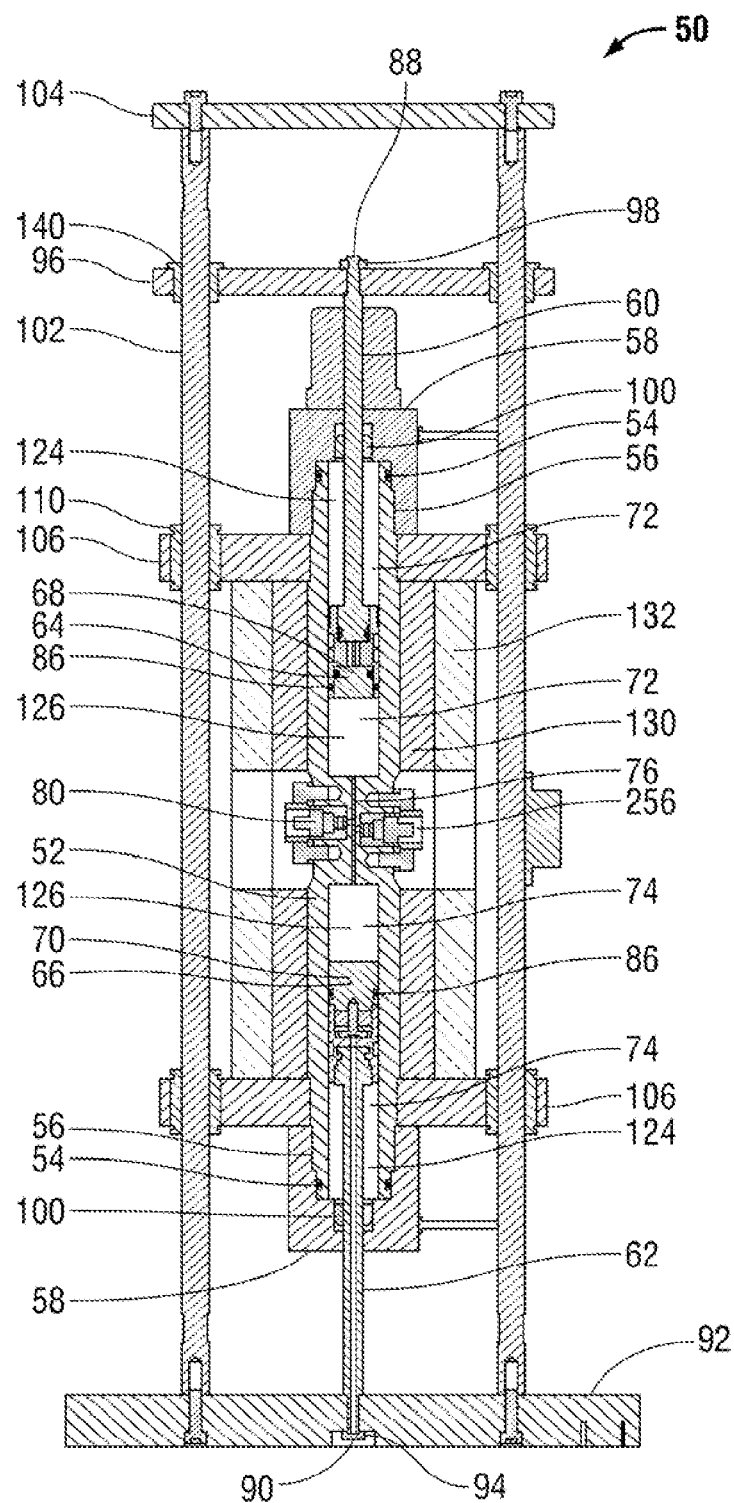
FIG. 15 is a schematic illustration of another example of a modular sensor assembly, according to an alternate embodiment of the present invention.

For example, modular sensor assembly 50 may be modified with an additional density-viscosity sensor 256, as illustrated in FIG. 15. The additional density-viscosity sensor 256 may comprise a specially designed resonator for measuring gas densities. In addition to knowing the total mass and/or total volume along with a liquid density and a gas density of a sample, it is possible to calculate the location of the gas-liquid interface, the error being dependent on the accuracies of the sensors. In some applications, the sensors, e.g. density-viscosity sensors 80, 256, may be provided with special coatings to prevent holdup of any one phase on its surfaces.

Figure 16:
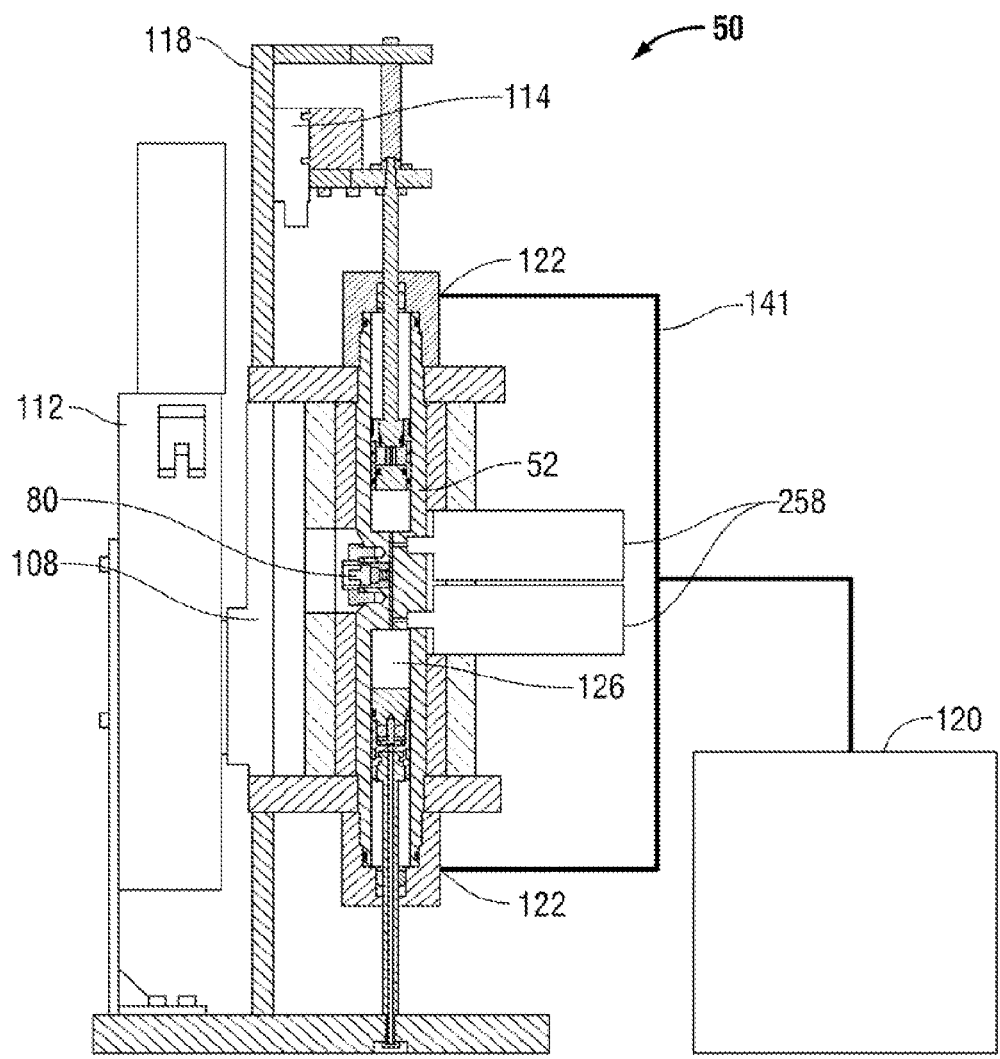
FIG. 16 is a schematic illustration of another example of a modular sensor assembly, according to an alternate embodiment of the present invention.

In another embodiment, the modular sensor assembly 50 may be modified with high pressure, high temperature (HPHT) sampling valves 258, as illustrated in FIG. 16. For example, sampling valves 258 may be of the ROLSI type, developed by the CENERG-TEP laboratory of the Ecole Nationale Superieure des Mines de Paris (ENSMP) (see U.S. Pat. No. 4,688,436) and sold under the Transvalor brand. This configuration allows for direct injection into a gas chromatograph. An advantage of these valves, as stated in U.S. Pat. No. 4,688,436, is that the sample withdrawn is small compared to the overall sample volume so that it does not disturb the equilibrium of the cell, hence improving experimental efficiency and allowing composition measurements to be made at a pressure and temperature giving more data than a regular CCE, i.e. the equivalent to a VLE (Vapour Liquid Equilibrium study). The sampling can also be done manually, but the HPHT valves allow the process to be automated. The sampling of these valves may be optimized for the operating range of pressures, temperatures, and viscosities of modular sensor assembly 50.

Figure 17:
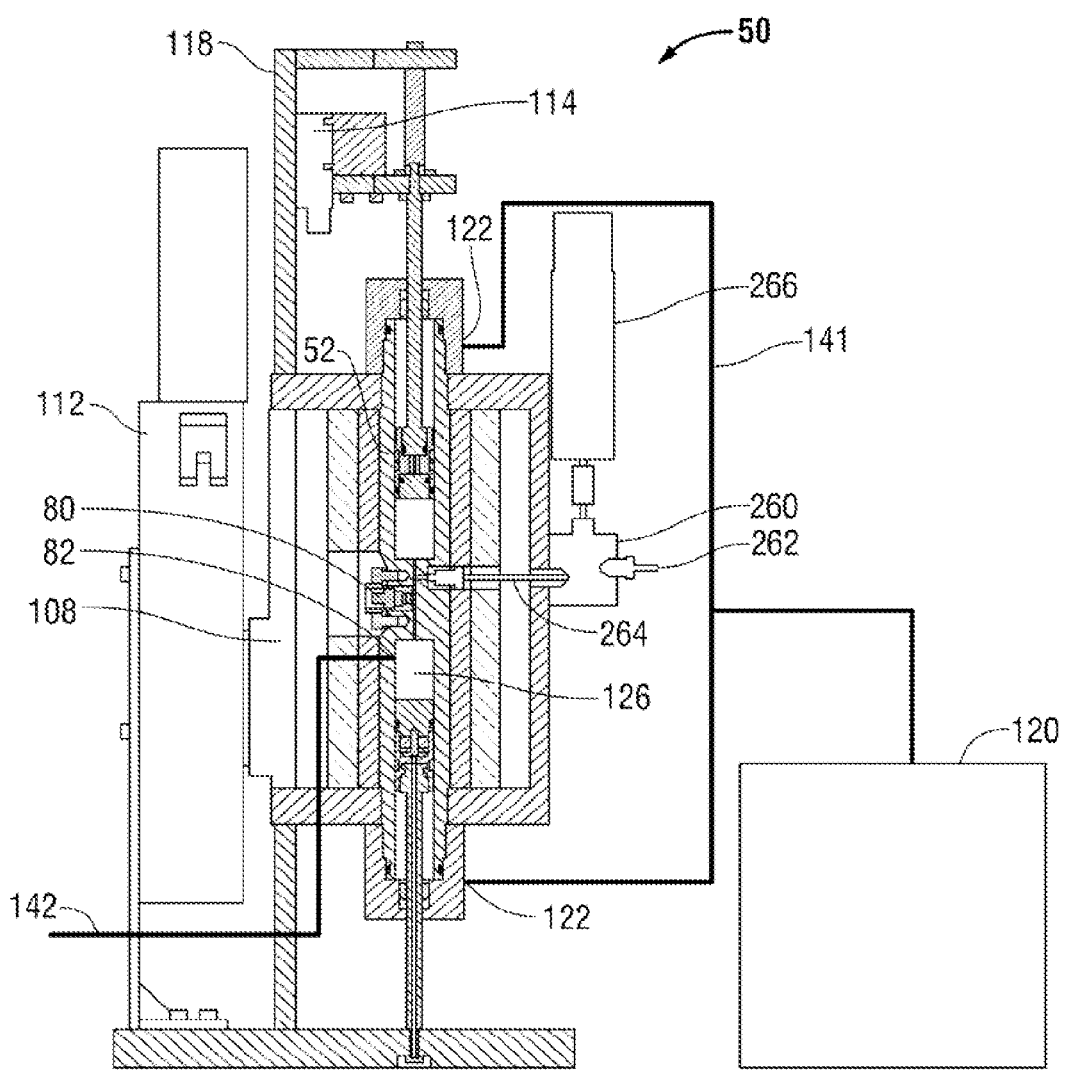
FIG. 17 is a schematic illustration of another example of a modular sensor assembly, according to an alternate embodiment of the present invention.

For lean condensates, modular sensor assembly 50 may be configured with an automated valve 260 to allow for liquid build-up described subsequently (see FIG. 17). At the temperature of interest, the sample (feed) is charged to the cell body 52 and then flashed to the pressure of interest. The resulting vapor phase and liquid phase are allowed to equilibrate and then the vapor phase is isobarically pushed from modular sensor assembly 50 through a line 262. Once all the vapor phase has been expelled from the cell body 52, additional feed is added to the cell at the feed conditions and then the mixture is allowed to equilibrate at the flash conditions. After equilibration, the vapor is isobarically pushed from the PVT cell. The process is repeated until a sufficient amount of liquid has been built up. Additional optical sensors 78 can be configured in the modular sensor assembly 50 or repositioned, if necessary, to increase accuracy of this process. In this embodiment, a coupler line 264 may be used to connect to valve 260 with a stepper motor 266. In this embodiment, stepper motor 266 is controlled, e.g. automatically controlled, by control system 134.

A variety of differing sensing principles may employ different types of sensors, such as acoustics sensors, capacitance sensors, nuclear density sensors, X-Ray sensors, etc., in place of the optic and/or density-viscosity sensors 78, 80 to make the same measurements. Also, the embodiments may be modified to make the device more easily operable or further customizable by, for example, allowing sensors to be optimized for specific ranges, if required.

Figure 18:
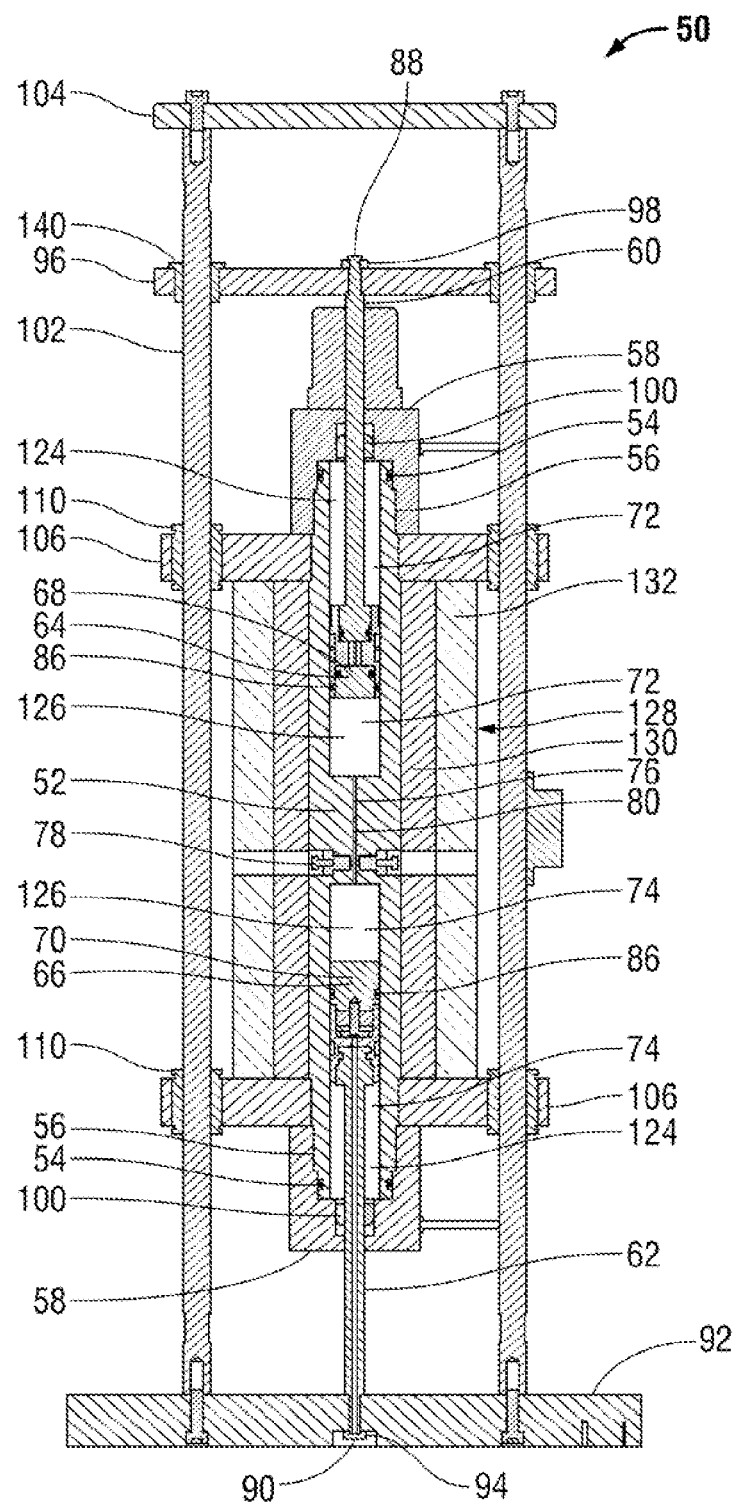
FIG. 18 is a schematic illustration of another example of a modular sensor assembly, according to an alternate embodiment of the present invention.
Figure 19:
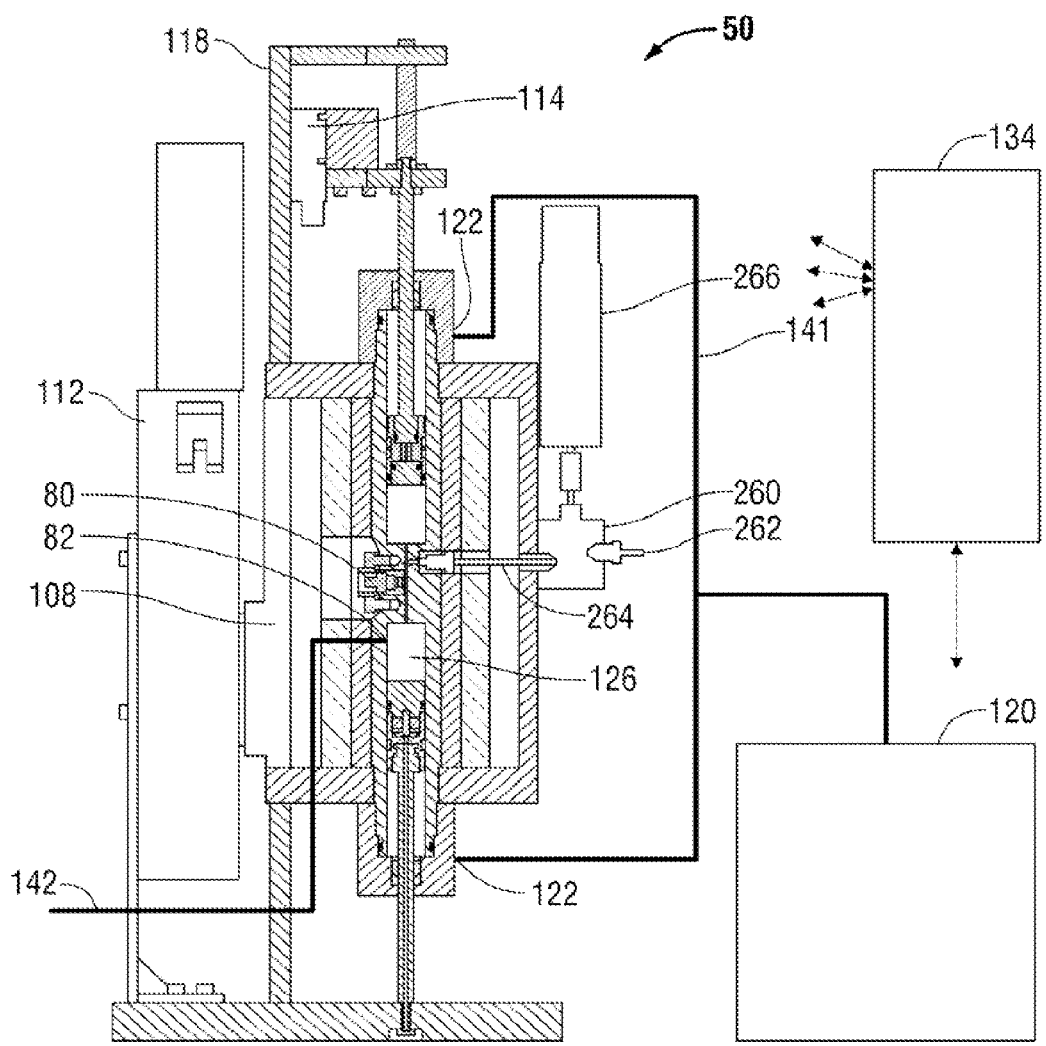
FIG. 19 is a schematic illustration of another example of a modular sensor assembly, according to an alternate embodiment of the present invention.
Figure 20:
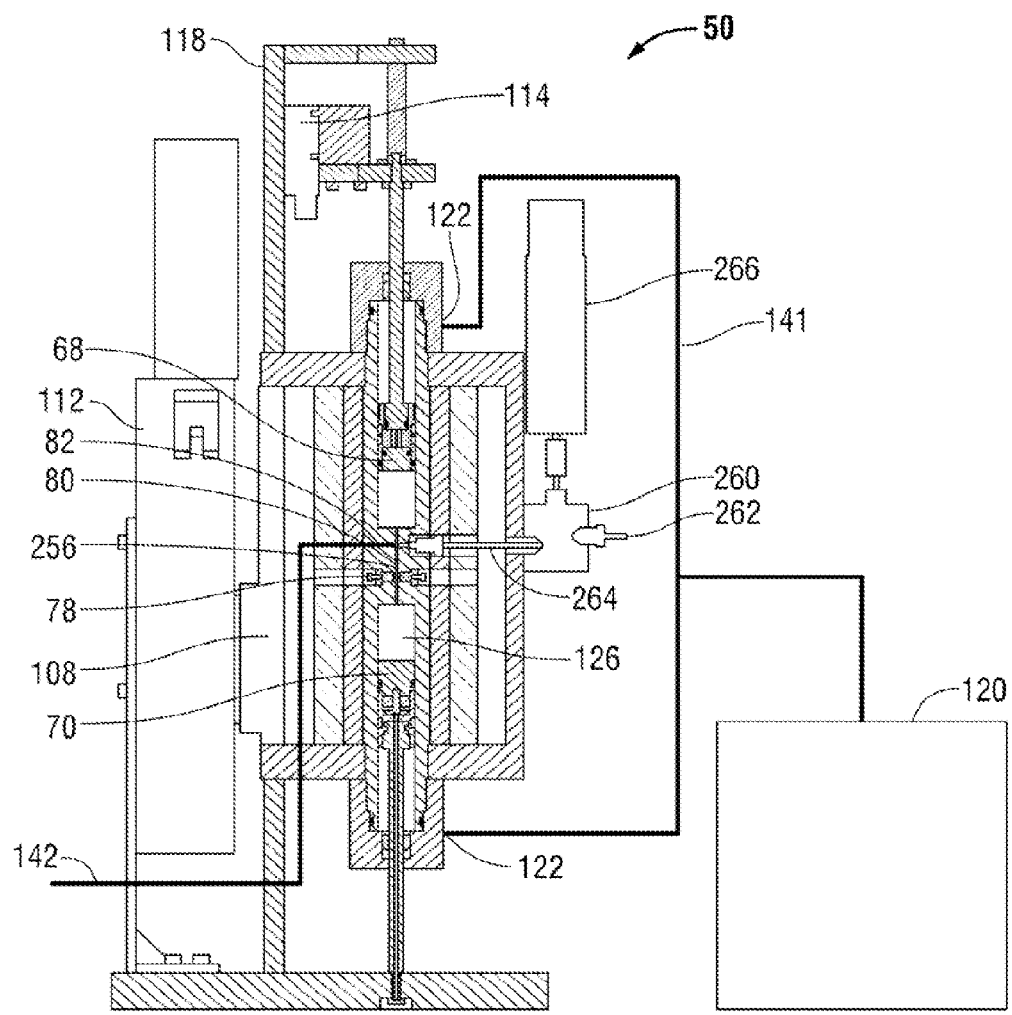
FIG. 20 is a schematic illustration of another example of a modular sensor assembly, according to an alternate embodiment of the present invention.

Other alternate embodiments or modifications may be made with respect to modular sensor assembly 50. Many of these embodiments may be similar to embodiments discussed above but with minor modifications to facilitate sampling and testing of specific fluids in specific environments. For example, FIGS. 18 and 19 illustrate an enhanced constant composition expansion (ECCE) condensate design having a single density-viscosity sensor, e.g. sensor 80. In this example, all testing functions, including charging the cell body 52, pressurizing the fluid sample, changing the temperature of the fluid sample, agitating the fluid sample, and utilizing the various sensors, may be fully automated under the control of processor based control system 134. In another, similar embodiment illustrated in FIG. 20, an ECCE condensate embodiment is illustrated as having two density-viscosity sensors, e.g. sensors 80 and 256.

Figure 21:
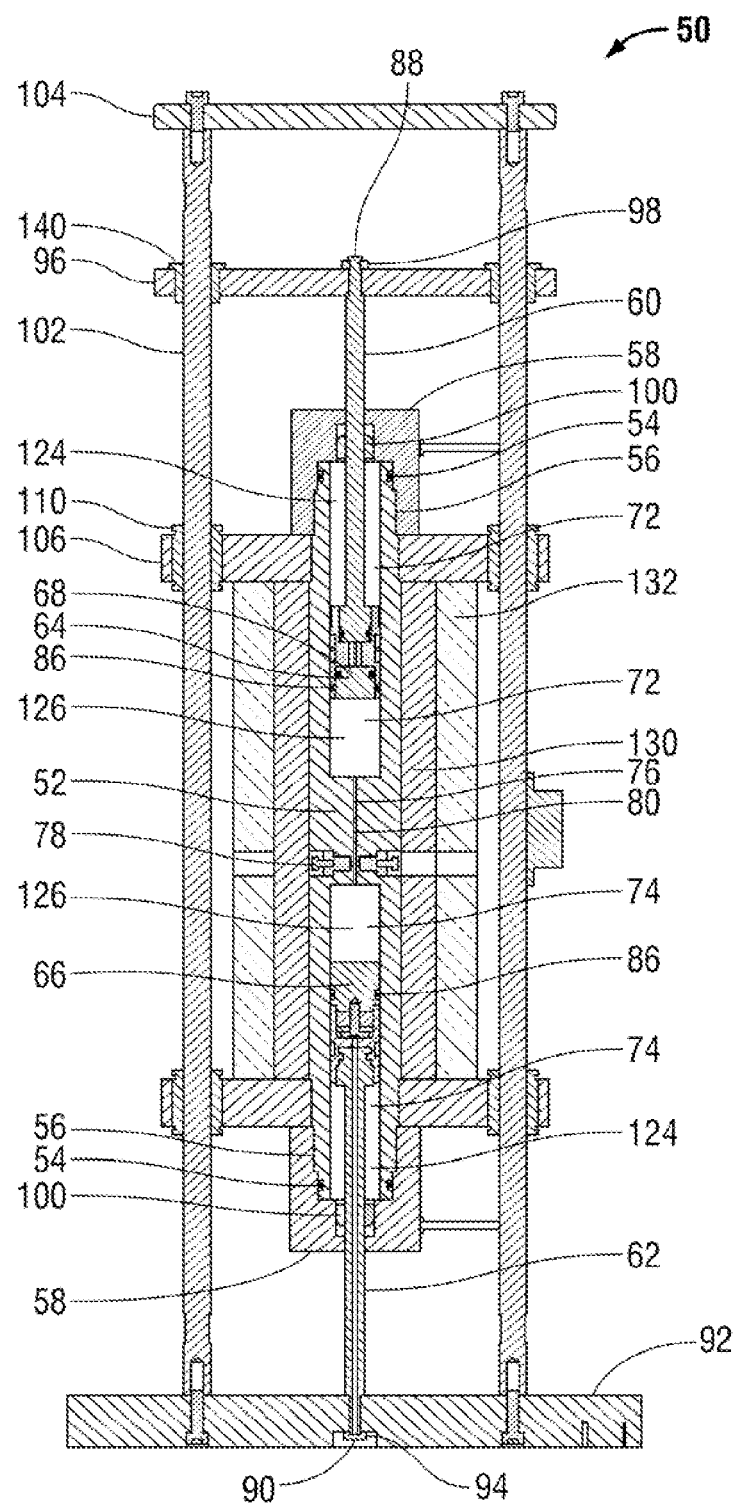
FIG. 21 is a schematic illustration of another example of a modular sensor assembly, according to an alternate embodiment of the present invention.
Figure 22:
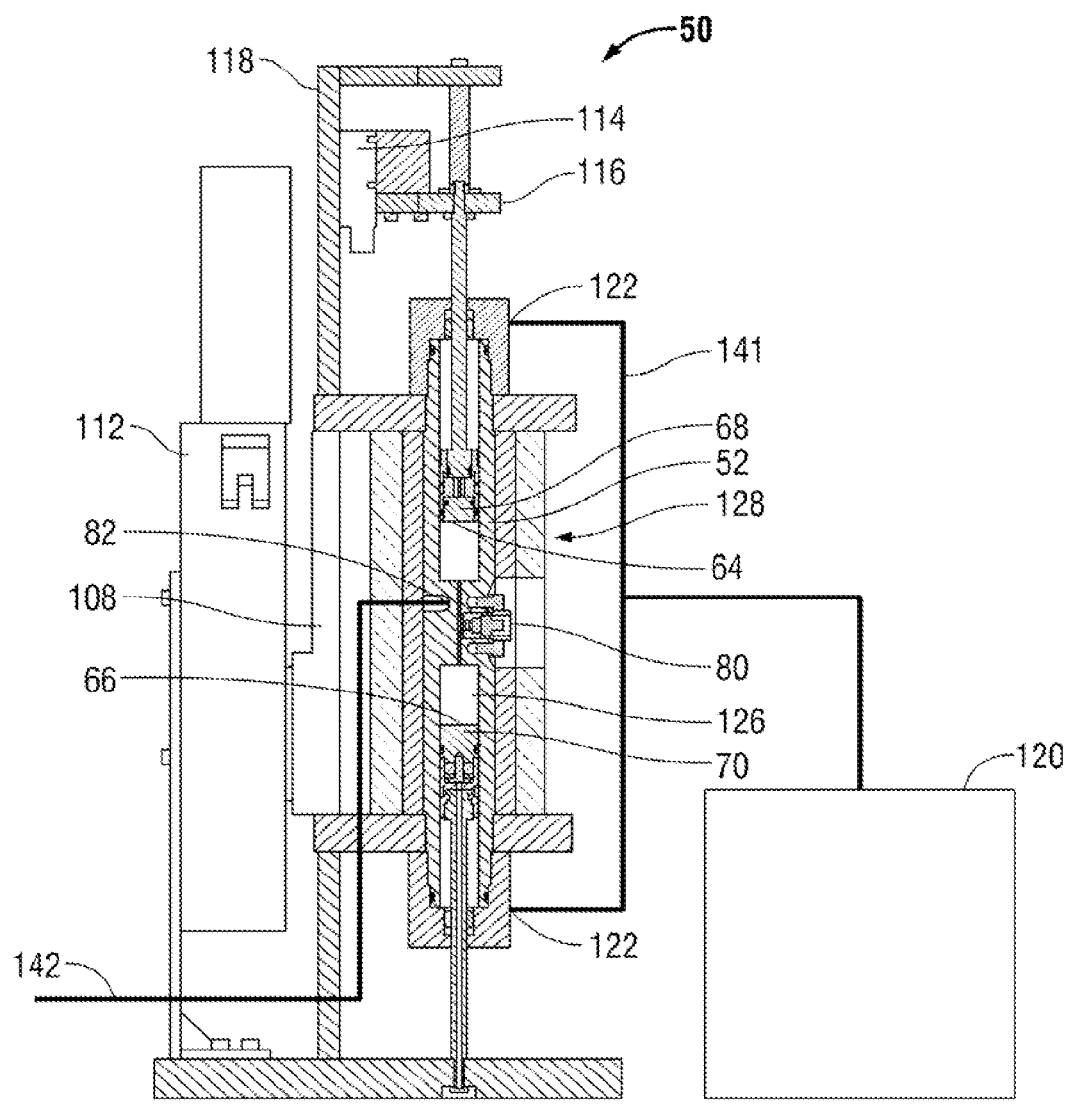
FIG. 22 is a schematic illustration of another example of a modular sensor assembly, according to an alternate embodiment of the present invention.
Figure 23:
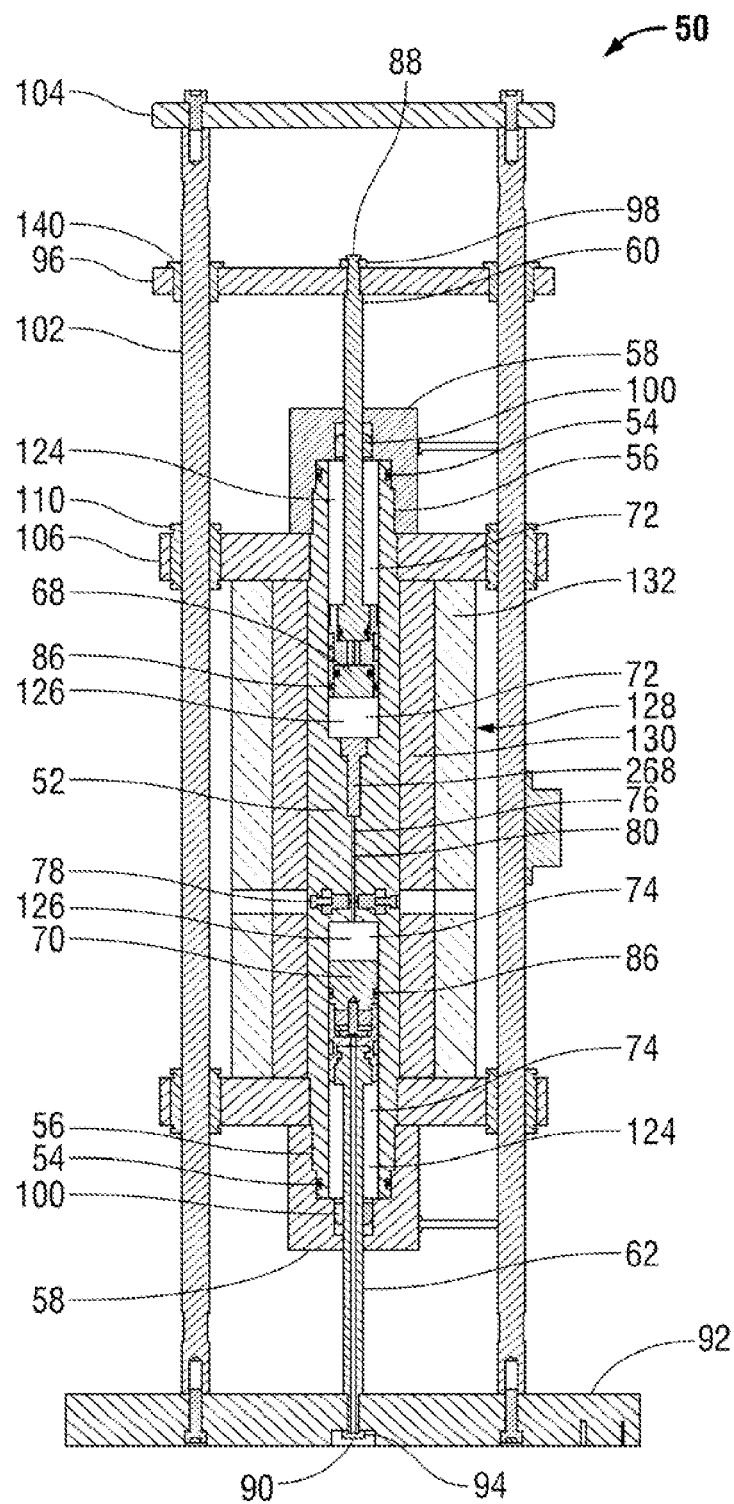
FIG. 23 is a schematic illustration of another example of a modular sensor assembly, according to an alternate embodiment of the present invention.
Figure 24:
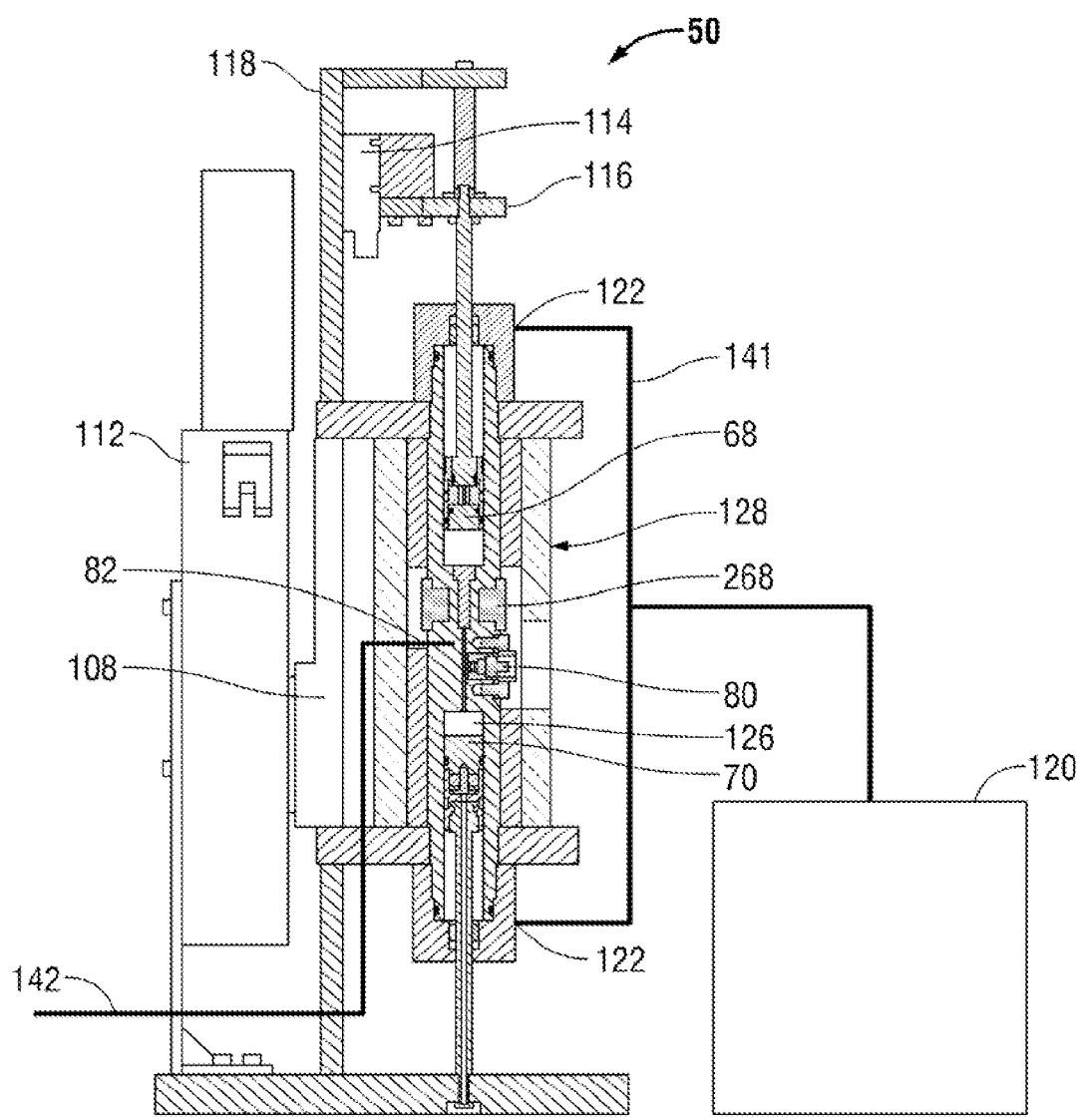
FIG. 24 is a schematic illustration of another example of a modular sensor assembly, according to an alternate embodiment of the present invention.

The modular sensor assembly 50 may also comprise different types of sampling chamber cylinders and different numbers of movable pistons. In FIGS. 21 and 22, for example, an embodiment is illustrated as an ECCE dual cylinder design having the single density-viscosity sensor 80. In this design, the pistons 68, 70 are each movable to adjust the fluid sample. Another embodiment is illustrated in FIGS. 23 and 24 which uses density-viscosity sensor 80 in combination with a vibrating wire viscosity sensor 268.

Figure 25:
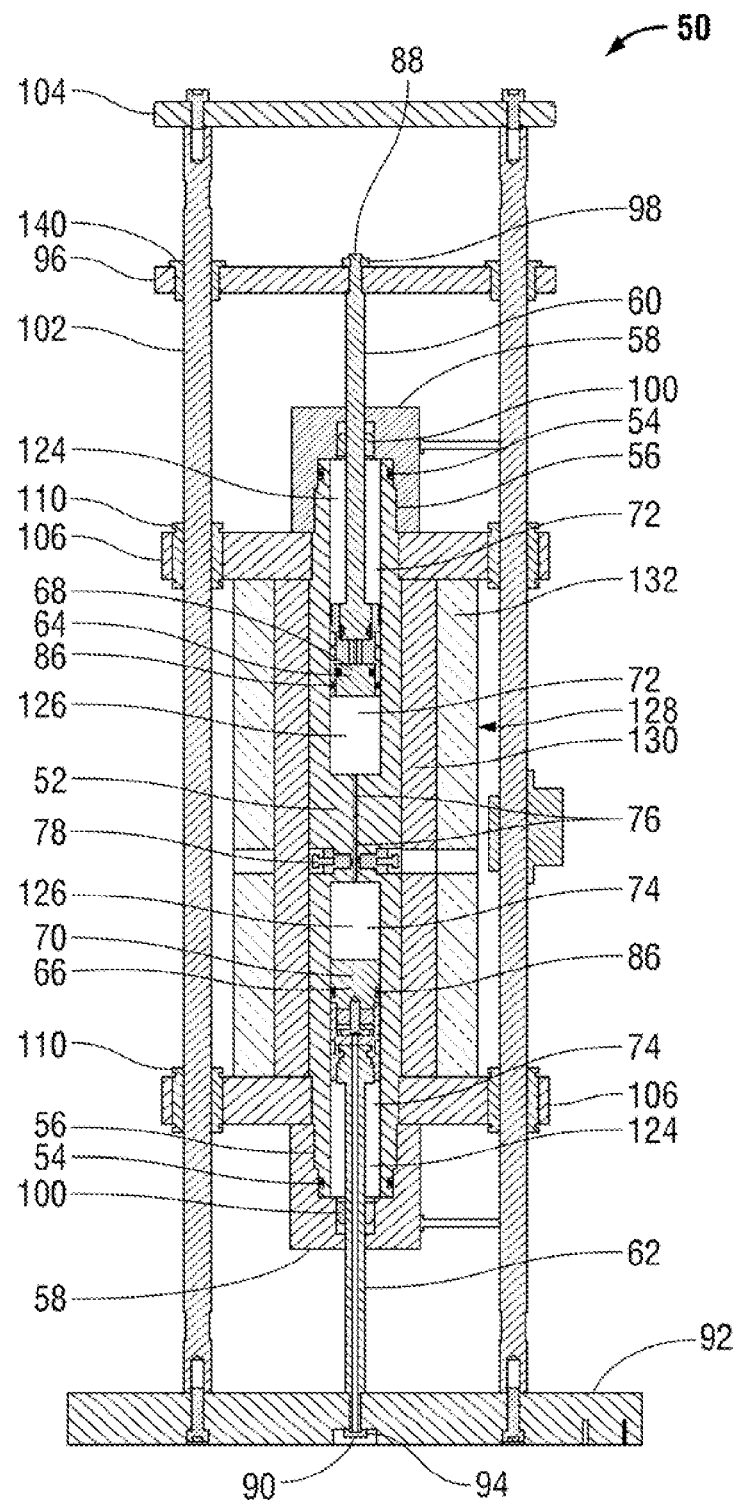
FIG. 25 is a schematic illustration of another example of a modular sensor assembly, according to an alternate embodiment of the present invention.
Figure 26:
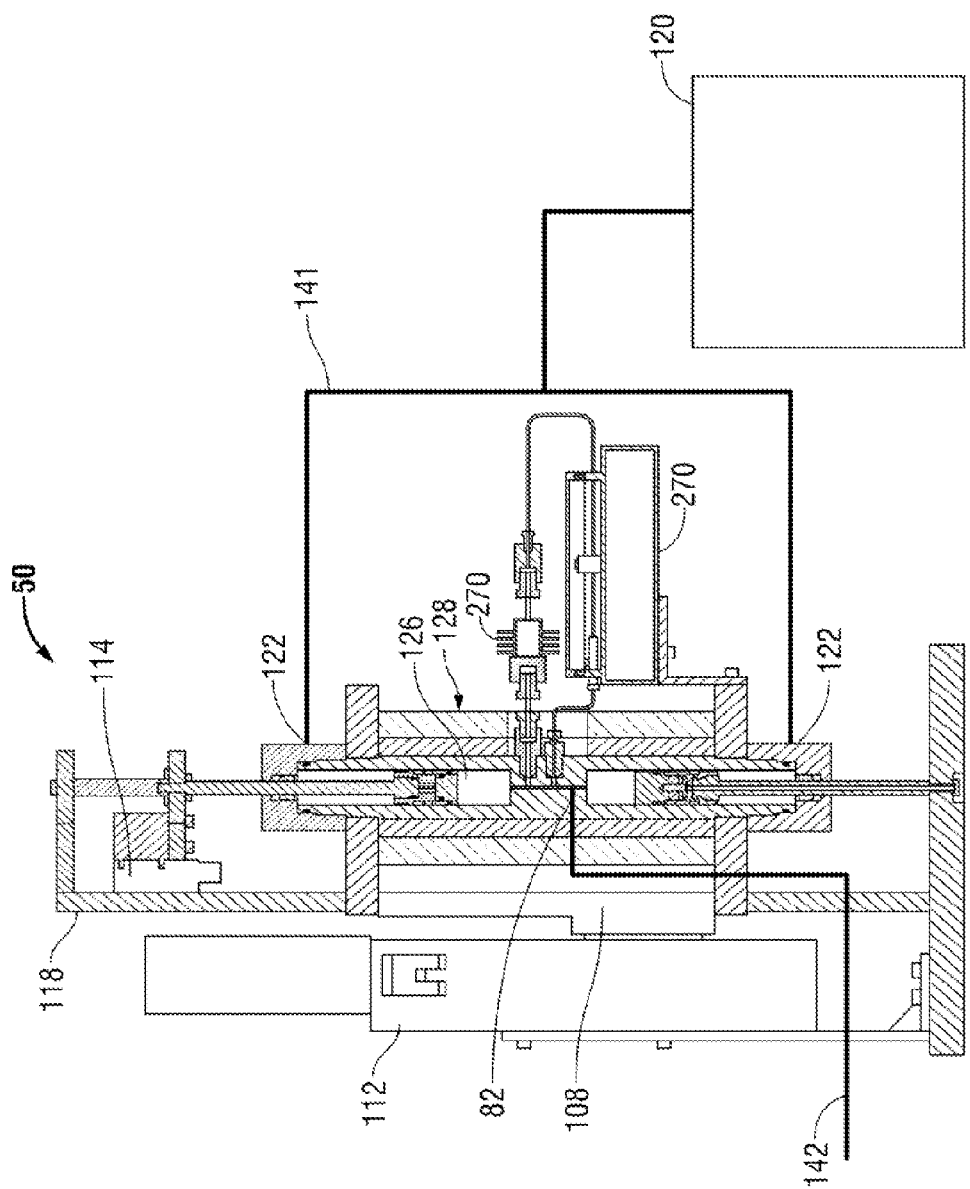
FIG. 26 is a schematic illustration of another example of a modular sensor assembly, according to an alternate embodiment of the present invention.
Figure 27:
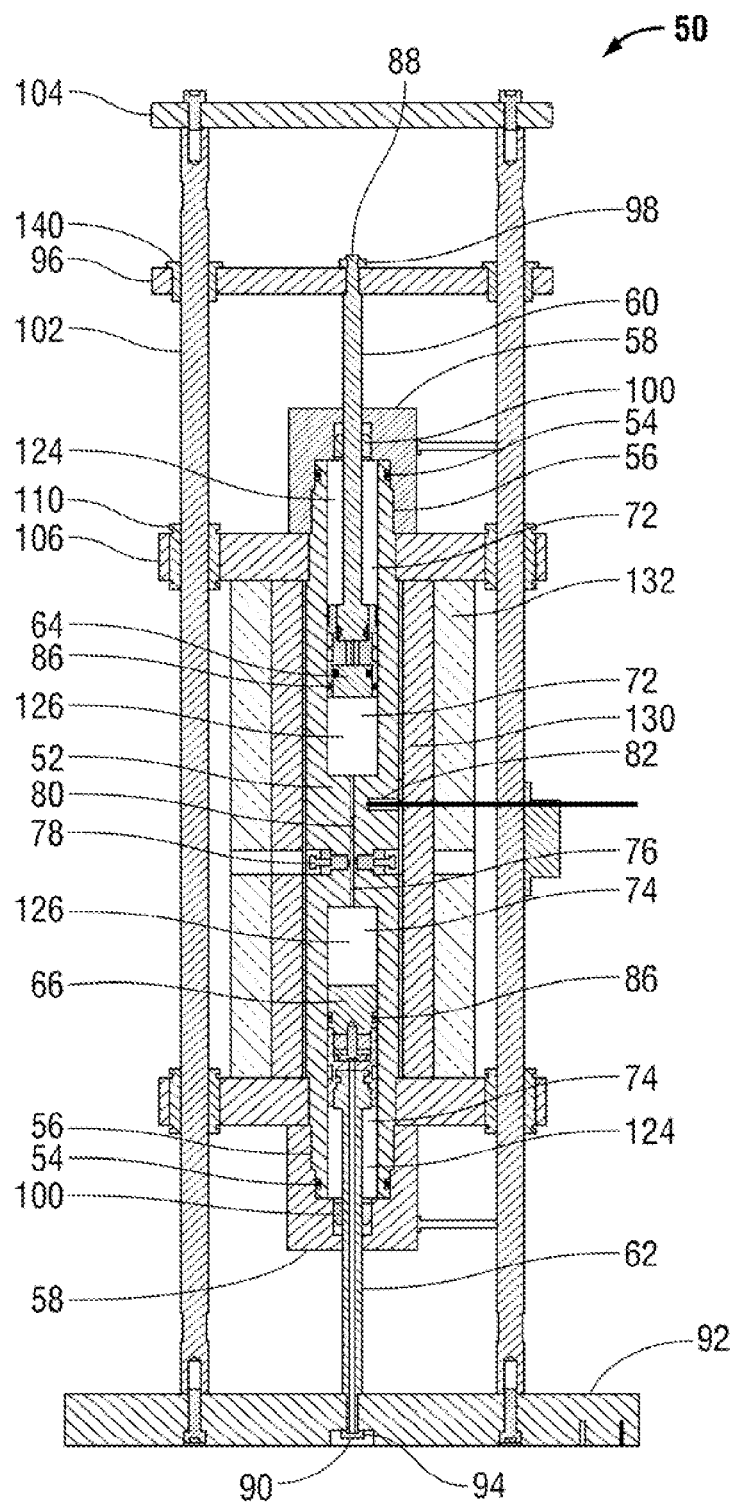
FIG. 27 is a schematic illustration of another example of a modular sensor assembly, according to an alternate embodiment of the present invention.
Figure 28:
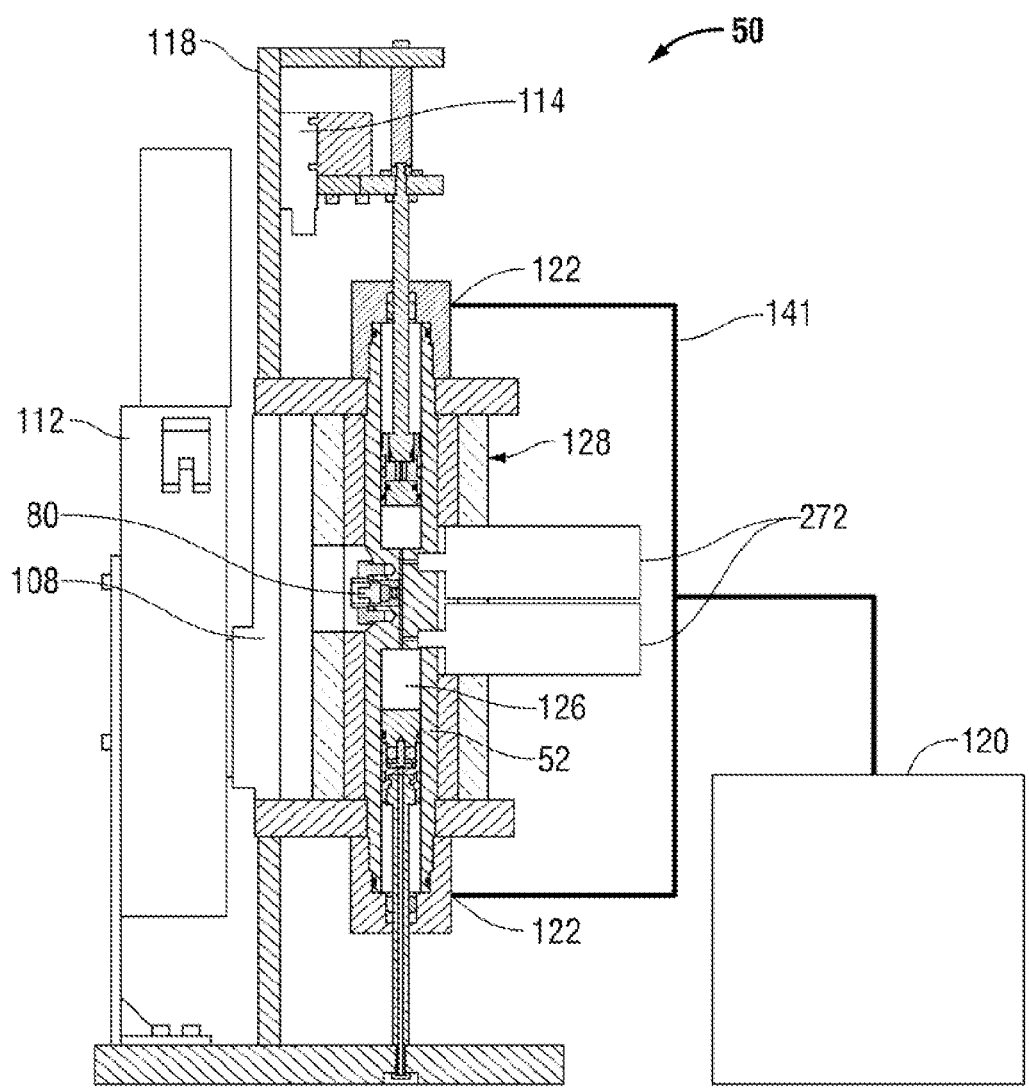
FIG. 28 is a schematic illustration of another example of a modular sensor assembly, according to an alternate embodiment of the present invention.

Other embodiments of modular sensor assembly 50 may incorporate alternate or additional sensors. For example, FIGS. 25 and 26 illustrate an ECCE dual cylinder embodiment having additional sensors 270, such as electromagnetic viscometer (EMV) sensors and/or vibrating tube densitometer (VTD) sensors. Another embodiment of modular sensor assembly 50 is illustrated in FIGS. 27 and 28 which shows an ECCE dual cylinder design with density-viscosity sensor 80 and additional valves 272, which may comprise ROLSI valves as discussed previously.

Figure 29:
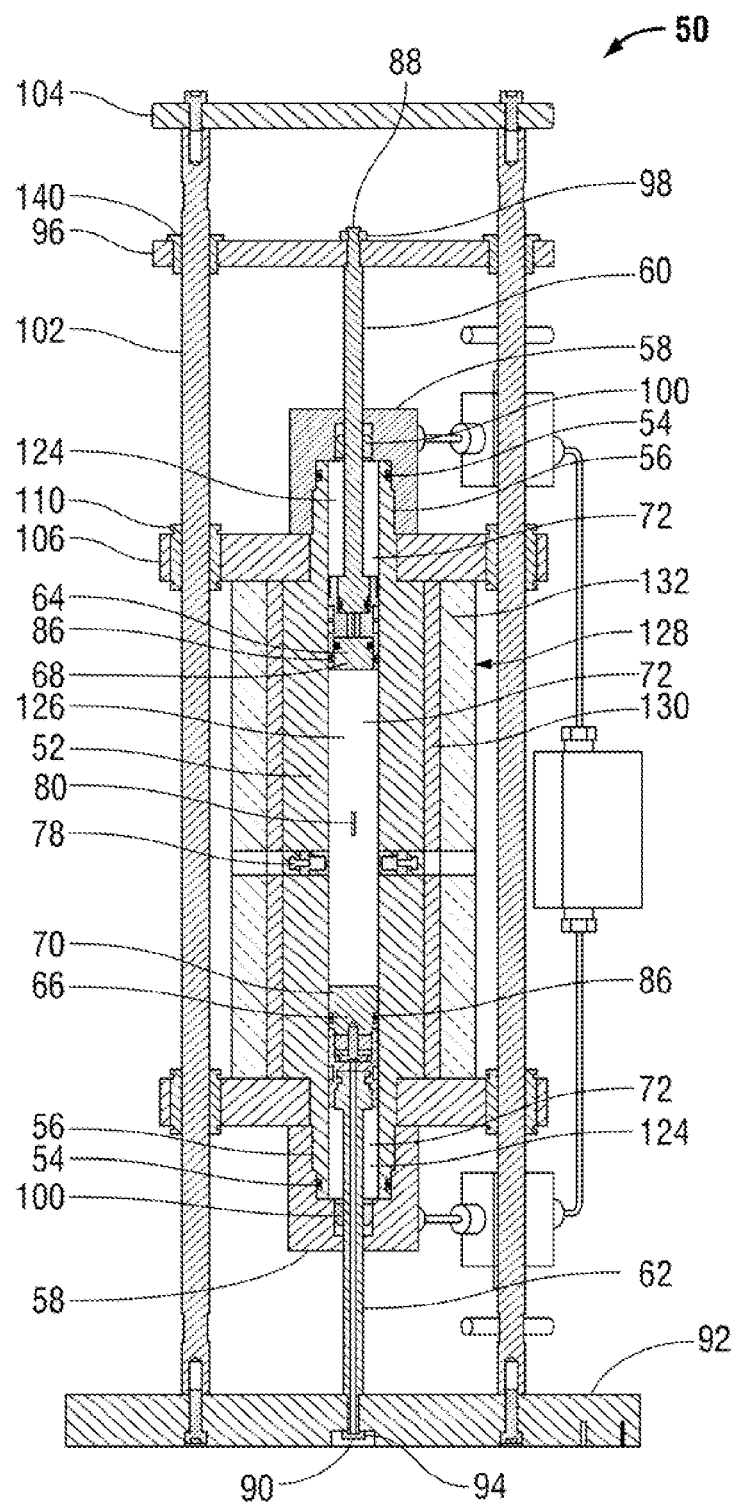
FIG. 29 is a schematic illustration of another example of a modular sensor assembly, according to an alternate embodiment of the present invention.
Figure 30:
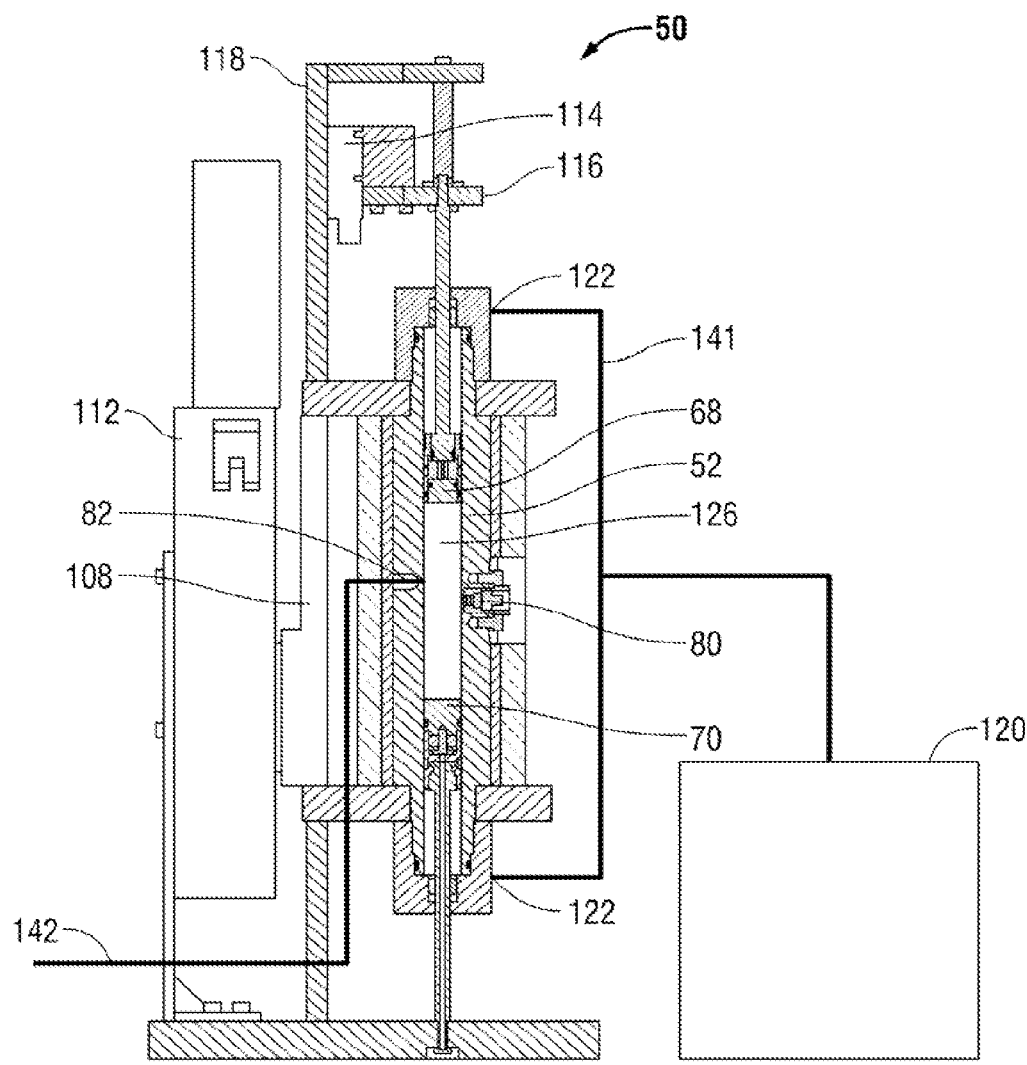
FIG. 30 is a schematic illustration of another example of a modular sensor assembly, according to an alternate embodiment of the present invention.

In FIGS. 29 and 30, another embodiment is illustrated in which the sample chamber 126 is designed as a single cylinder having dual pistons, e.g. pistons 68, 70, which cooperate with a single density-viscosity sensor 80. A related embodiment comprises the single cylinder/dual piston design but with two density-viscosity sensors, e.g. sensors 80 and 256. FIGS. 15-30 provide just a few examples of alternate embodiments and modifications which may be made to the embodiments to facilitate sample testing with a modular system as described above. Other configurations of the cell body 52 may be utilized, and a variety of sensors and other components may be removed, added, or substituted as desired for a given application.

Accordingly, although only a few embodiments of the present invention have been described in detail above, those of ordinary skill in the art will readily appreciate that many modifications are possible without materially departing from the teachings of this invention.

What is claimed is:

1. An apparatus for measuring thermodynamic properties of reservoir fluids, comprising:
a modular sensor assembly comprising a cell body having a sample chamber for receiving a sample of single phase or coexisting two-phase fluid, an agitation mechanism to agitate the sample in the sample chamber, and a density-viscosity sensor located in-situ to measure the density and viscosity of the sample in the sample chamber as a function of pressure and temperature.

2. The apparatus as recited in claim 1, wherein the agitation mechanism comprises an ultrasonic transducer.

3. A method of measuring thermodynamic properties of reservoir fluids, comprising:
assembling a modular sensor assembly to evaluate a sample of a hydrocarbon-containing fluid;
charging a sample chamber within a cell body of the modular sensor assembly with the sample;
adjusting the temperature and the pressure of the sample within the sample chamber; and
utilizing a single sensor to determine both density and viscosity of the sample while in the sample chamber.

4. The method as recited in claim 3, further comprising using an optic sensor to measure parameters of the sample while in the sample chamber.

5. The method as recited in claim 3, further comprising adjusting the pressure of the sample in the sample chamber with a piston.

6. The method as recited in claim 3, further comprising adjusting the temperature of the sample in the sample chamber with a thermal management system surrounding the cell body.

7. The method as recited in claim 3, further comprising automatically controlling the charging, adjusting, and utilizing steps with a processor-based controller.

8. A method of measuring thermodynamic properties of reservoir fluids, comprising:
providing a portable, modular sensor assembly at a wellsite;
charging a cell body of the portable, modular sensor assembly with a fluid sample from a subterranean reservoir;
pressurizing the fluid sample within the cell body by compressing the fluid sample while in the cell body;
increasing the temperature of the fluid sample with a thermal management system positioned as an integral part of the portable, modular sensor assembly;
agitating the fluid sample while in the cell body to recombine fluid from multiple phases into a single phase; and
utilizing sensors exposed to an inner sample chamber of the cell body to measure desired properties of the fluid sample.

9. The method as recited in claim 8, further comprising utilizing a processor-based control system to automate the charging, pressurizing, increasing, agitating, and utilizing steps.

10. The method as recited in claim 8, wherein utilizing sensors comprises utilizing a single density-viscosity sensor.

11. The method as recited in claim 8, wherein utilizing sensors comprises utilizing a plurality of density-viscosity sensors.

12. The method as recited in claim 8, wherein utilizing sensors comprises utilizing an optic sensor.

* * * * *

UNITED STATES PATENT AND TRADEMARK OFFICE
CERTIFICATE OF CORRECTION

PATENT NO. : 9,291,585 B2
APPLICATION NO. : 13/818996
DATED : March 22, 2016
INVENTOR(S) : Anil Singh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 598 days.

Signed and Sealed this
Second Day of August, 2016

Michelle K. Lee
*Director of the United States Patent and Trademark Office*